United States Patent
Gorensek et al.

(10) Patent No.: US 7,500,978 B2
(45) Date of Patent: Mar. 10, 2009

(54) METHOD FOR DELIVERING AND POSITIONING IMPLANTS IN THE INTERVERTEBRAL DISC ENVIRONMENT

(75) Inventors: Bogomir Gorensek, Ljubljana (SI); Gregory H. Lambrecht, Natick, MA (US); Sean Kavanaugh, Eastham, MA (US); Robert Kevin Moore, Natick, MA (US)

(73) Assignee: Intrinsic Therapeutics, Inc., Woburn, MA (US)

( * ) Notice: Subject to any disclaimer, the term of this patent is extended or adjusted under 35 U.S.C. 154(b) by 0 days.

(21) Appl. No.: 11/478,777

(22) Filed: Jun. 30, 2006

(65) Prior Publication Data

US 2006/0247785 A1 Nov. 2, 2006

Related U.S. Application Data

(63) Continuation of application No. 10/873,074, filed on Jun. 21, 2004.

(60) Provisional application No. 60/480,276, filed on Jun. 20, 2003.

(51) Int. Cl.
*A61B 17/58* (2006.01)
*A61B 17/60* (2006.01)
*A61F 2/00* (2006.01)

(52) U.S. Cl. .................. 606/99; 606/246; 606/279; 623/17.11

(58) Field of Classification Search .......... 623/17.11, 623/17.13, 1.11; 606/60, 72, 74, 75, 78, 606/99, 53, 86, 213, 215, 219, 221
See application file for complete search history.

(56) References Cited

U.S. PATENT DOCUMENTS

| | | | |
|---|---|---|---|
| 3,526,567 A | 9/1970 | Macone | |
| 3,867,728 A | 2/1975 | Stubstad et al. | |
| 3,875,595 A | 4/1975 | Froning | |
| 3,921,632 A | 11/1975 | Bardani | |

(Continued)

FOREIGN PATENT DOCUMENTS

EP 0298233 1/1989

(Continued)

OTHER PUBLICATIONS

Bagga C.S. Williams P. Highma P.A. Bao B.Q. "Development of Fatigue Test Model for a Spinal Nucleus Prosthesis with Preliminary Results for a Hydrogel Spinal Prosthetic Nucleus." Proceedings of the 1997 Bioengineering Conference 441-442: BED-vol. 35 Sunriver Oregon Jun. 11-15, 1997.

(Continued)

*Primary Examiner*—Eduardo C Robert
*Assistant Examiner*—Andrew Yang
(74) *Attorney, Agent, or Firm*—Knobbe, Martens, Olson & Bear, LLP; Sean Kavanaugh

(57) ABSTRACT

The present invention relates generally to devices and methods for delivering medical devices, such as implants, to desired tissue sites, such as the intervertebral disc. In one aspect, an intervertebral disc repair and diagnostic device that is minimally invasive and that provides precise access to the desired site is provided. In some aspects, the device and method are adapted to deliver, position and expand implants that are initially oriented and compressed for minimally invasive, yet precise and effective implantation.

16 Claims, 23 Drawing Sheets

U.S. PATENT DOCUMENTS

| | | |
|---|---|---|
| 4,349,921 A | 9/1982 | Kuntz |
| 4,473,070 A | 9/1984 | Matthews et al. |
| 4,502,161 A | 3/1985 | Wall |
| 4,532,926 A | 8/1985 | O'Holla |
| 4,665,906 A | 5/1987 | Jervis |
| 4,741,330 A | 5/1988 | Hayhurst |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,821,942 A | 4/1989 | Richards et al. |
| 4,837,285 A | 6/1989 | Berg et al. |
| 4,852,568 A | 8/1989 | Kensey |
| 4,863,477 A | 9/1989 | Monson |
| 4,871,094 A | 10/1989 | Gall et al. |
| 4,873,976 A | 10/1989 | Schreiber |
| 4,890,612 A | 1/1990 | Kensey |
| 4,904,260 A | 2/1990 | Ray et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,021,059 A | 6/1991 | Kensey et al. |
| 5,035,716 A | 7/1991 | Downey |
| 5,047,055 A | 9/1991 | Bao et al. |
| 5,053,046 A | 10/1991 | Janese |
| 5,059,206 A | 10/1991 | Winters |
| 5,061,274 A | 10/1991 | Kensey |
| 5,071,437 A | 12/1991 | Steffee |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,155 A | 6/1992 | Eberbach |
| 5,123,926 A | 6/1992 | Pisharodi |
| 5,129,906 A | 7/1992 | Ross et al. |
| 5,141,515 A | 8/1992 | Eberbach |
| 5,147,374 A | 9/1992 | Fernandez |
| 5,171,252 A | 12/1992 | Friedland |
| 5,171,259 A | 12/1992 | Inoue |
| 5,171,280 A | 12/1992 | Baumgartner |
| 5,171,281 A | 12/1992 | Parsons et al. |
| 5,176,692 A | 1/1993 | Wilk et al. |
| 5,189,789 A | 3/1993 | Hall |
| 5,192,300 A | 3/1993 | Fowler |
| 5,192,301 A | 3/1993 | Kamiya et al. |
| 5,192,326 A | 3/1993 | Bao et al. |
| 5,201,729 A | 4/1993 | Hertzmann et al. |
| 5,207,649 A | 5/1993 | Aruny |
| 5,219,359 A | 6/1993 | McQuilkin et al. |
| 5,222,974 A | 6/1993 | Kensey et al. |
| 5,239,982 A | 8/1993 | Trauthen |
| 5,242,448 A | 9/1993 | Pettine et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,282,827 A | 2/1994 | Kensey et al. |
| 5,292,332 A | 3/1994 | Lee |
| 5,306,311 A | 4/1994 | Stone et al. |
| 5,312,435 A | 5/1994 | Nash et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,356,432 A | 10/1994 | Rutkow et al. |
| 5,366,460 A | 11/1994 | Eberbach |
| 5,368,602 A | 11/1994 | De la Torre |
| 5,370,697 A | 12/1994 | Baumgartner |
| 5,383,477 A | 1/1995 | DeMatteis |
| 5,383,905 A | 1/1995 | Golds et al. |
| 5,397,331 A | 3/1995 | Himpens et al. |
| 5,397,332 A | 3/1995 | Kammerer et al. |
| 5,397,355 A | 3/1995 | Marin et al. |
| 5,405,360 A | 4/1995 | Tovey |
| 5,425,773 A | 6/1995 | Boyd et al. |
| 5,437,631 A | 8/1995 | Janzen |
| 5,445,639 A | 8/1995 | Kuslich et al. |
| 5,456,720 A | 10/1995 | Schultz |
| 5,464,407 A | 11/1995 | McGuire |
| 5,500,000 A | 3/1996 | Feagin et al. |
| 5,507,754 A | 4/1996 | Green et al. |
| 5,514,130 A | 5/1996 | Baker |
| 5,514,180 A | 5/1996 | Heggeness et al. |
| 5,520,700 A | 5/1996 | Beyar et al. |
| 5,522,898 A | 6/1996 | Bao |
| 5,531,759 A | 7/1996 | Kensey et al. |
| 5,534,028 A | 7/1996 | Bao et al. |
| 5,534,030 A | 7/1996 | Navarro et al. |
| 5,545,178 A | 8/1996 | Kensey et al. |
| 5,545,229 A | 8/1996 | Parsons et al. |
| 5,549,617 A | 8/1996 | Green et al. |
| 5,549,679 A | 8/1996 | Kuslich |
| 5,552,100 A | 9/1996 | Shannon et al. |
| 5,556,428 A | 9/1996 | Shah |
| 5,556,429 A | 9/1996 | Felt |
| 5,562,689 A | 10/1996 | Green et al. |
| 5,562,736 A | 10/1996 | Ray |
| 5,562,738 A | 10/1996 | Boyd et al. |
| 5,569,252 A | 10/1996 | Justin et al. |
| 5,571,189 A | 11/1996 | Kuslich |
| 5,582,616 A | 12/1996 | Bolduc et al. |
| 5,591,204 A | 1/1997 | Janzen et al. |
| 5,591,223 A | 1/1997 | Lock et al. |
| 5,613,974 A | 3/1997 | Andreas et al. |
| 5,620,012 A | 4/1997 | Benderev et al. |
| 5,624,463 A | 4/1997 | Stone et al. |
| 5,626,613 A | 5/1997 | Schmieding |
| 5,634,931 A | 6/1997 | Kugel |
| 5,634,936 A | 6/1997 | Linden et al. |
| 5,641,373 A | 6/1997 | Shannon et al. |
| 5,645,084 A | 7/1997 | McKay |
| 5,645,597 A | 7/1997 | Krapiva |
| 5,658,343 A | 8/1997 | Hauselmann et al. |
| 5,662,683 A | 9/1997 | Kay |
| 5,669,935 A | 9/1997 | Rosenman et al. |
| 5,674,294 A | 10/1997 | Bainville et al. |
| 5,674,295 A | 10/1997 | Ray et al. |
| 5,674,296 A | 10/1997 | Bryan et al. |
| 5,676,698 A | 10/1997 | Janzen et al. |
| 5,676,701 A | 10/1997 | Yuan et al. |
| 5,681,351 A | 10/1997 | Jamiolkowski |
| 5,683,465 A | 11/1997 | Shinn et al. |
| 5,690,674 A | 11/1997 | Diaz |
| 5,695,525 A | 12/1997 | Mulhauser et al. |
| 5,702,450 A | 12/1997 | Bisserie |
| 5,702,451 A | 12/1997 | Biedermann et al. |
| 5,702,454 A | 12/1997 | Baumgartner |
| 5,702,462 A | 12/1997 | Oberlander |
| 5,705,780 A | 1/1998 | Bao |
| 5,716,408 A | 2/1998 | Eldridge et al. |
| 5,716,409 A | 2/1998 | Debbas |
| 5,716,413 A | 2/1998 | Walter et al. |
| 5,716,416 A | 2/1998 | Lin |
| 5,725,577 A | 3/1998 | Saxon |
| 5,728,150 A | 3/1998 | McDonald et al. |
| 5,730,744 A | 3/1998 | Justin et al. |
| 5,733,337 A | 3/1998 | Carr, Jr. et al. |
| 5,743,917 A | 4/1998 | Saxon |
| 5,746,755 A | 5/1998 | Wood et al. |
| 5,746,765 A | 5/1998 | Kleshinski et al. |

| Patent | Date | Name |
|---|---|---|
| 5,755,797 A | 5/1998 | Baumgartner |
| 5,766,246 A | 6/1998 | Mulhauser et al. |
| 5,769,864 A | 6/1998 | Kugel |
| 5,769,893 A | 6/1998 | Shah |
| 5,772,661 A | 6/1998 | Michelson |
| 5,776,183 A | 7/1998 | Kanesaka et al. |
| 5,782,844 A | 7/1998 | Yoon et al. |
| 5,785,705 A | 7/1998 | Baker |
| 5,800,549 A | 9/1998 | Bao et al. |
| 5,810,851 A | 9/1998 | Yoon |
| 5,823,994 A | 10/1998 | Sharkey et al. |
| 5,824,008 A | 10/1998 | Bolduc et al. |
| 5,824,082 A | 10/1998 | Brown |
| 5,824,093 A | 10/1998 | Ray et al. |
| 5,824,094 A | 10/1998 | Serhan et al. |
| 5,827,298 A | 10/1998 | Hart et al. |
| 5,836,315 A | 11/1998 | Benderev et al. |
| 5,843,084 A | 12/1998 | Hart et al. |
| 5,843,173 A | 12/1998 | Shannon et al. |
| 5,846,261 A | 12/1998 | Kotula et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,888,220 A | 3/1999 | Felt et al. |
| 5,888,226 A | 3/1999 | Rogozinski |
| 5,893,889 A | 4/1999 | Harrington |
| 5,916,225 A | 6/1999 | Kugel |
| 5,919,235 A | 7/1999 | Husson et al. |
| 5,922,026 A | 7/1999 | Chin |
| 5,928,279 A | 7/1999 | Shannon et al. |
| 5,928,284 A | 7/1999 | Mehdizadeh |
| 5,935,147 A | 8/1999 | Kensey et al. |
| 5,954,716 A | 9/1999 | Sharkey et al. |
| 5,954,767 A | 9/1999 | Pajotin et al. |
| 5,957,939 A | 9/1999 | Heaven et al. |
| 5,961,545 A | 10/1999 | Lentz et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,976,192 A | 11/1999 | McIntyre et al. |
| 5,980,504 A | 11/1999 | Sharkey et al. |
| 6,001,056 A | 12/1999 | Jassawalla et al. |
| 6,001,130 A | 12/1999 | Bryan et al. |
| 6,007,570 A | 12/1999 | Sharkey et al. |
| 6,007,575 A | 12/1999 | Samuels |
| 6,019,793 A | 2/2000 | Perren et al. |
| 6,024,096 A | 2/2000 | Buckberg |
| 6,027,527 A | 2/2000 | Asano et al. |
| 6,073,051 A | 6/2000 | Sharkey et al. |
| 6,096,044 A | 8/2000 | Boyd et al. |
| 6,099,791 A | 8/2000 | Shannon et al. |
| 6,102,930 A | 8/2000 | Simmons, Jr. |
| 6,105,581 A | 8/2000 | Eggers et al. |
| 6,113,639 A | 9/2000 | Ray et al. |
| 6,120,539 A | 9/2000 | Eldridge et al. |
| 6,124,523 A | 9/2000 | Banas et al. |
| 6,126,682 A | 10/2000 | Sharkey et al. |
| 6,132,465 A | 10/2000 | Ray et al. |
| 6,140,452 A | 10/2000 | Felt et al. |
| 6,146,380 A | 11/2000 | Racz et al. |
| 6,153,292 A * | 11/2000 | Bell et al. ............... 428/305.5 |
| 6,174,311 B1 | 1/2001 | Branch et al. |
| 6,179,836 B1 | 1/2001 | Eggers et al. |
| 6,183,518 B1 | 2/2001 | Ross et al. |
| 6,187,048 B1 | 2/2001 | Milner et al. |
| 6,190,353 B1 | 2/2001 | Makower et al. |
| 6,203,735 B1 | 3/2001 | Edwin et al. |
| 6,206,921 B1 | 3/2001 | Guagliano et al. |
| 6,214,039 B1 | 4/2001 | Banas et al. |
| 6,224,630 B1 | 5/2001 | Bao et al. |
| 6,224,631 B1 | 5/2001 | Kohrs |
| 6,231,597 B1 | 5/2001 | Deem et al. |
| 6,241,722 B1 | 6/2001 | Dobak et al. |
| 6,245,099 B1 | 6/2001 | Edwin et al. |
| 6,245,107 B1 | 6/2001 | Ferree |
| 6,264,659 B1 | 7/2001 | Ross et al. |
| 6,264,695 B1 | 7/2001 | Stoy |
| 6,267,834 B1 | 7/2001 | Shannon et al. |
| 6,273,912 B1 | 8/2001 | Scholz et al. |
| 6,280,475 B1 | 8/2001 | Bao et al. |
| 6,312,462 B1 | 11/2001 | McDermott et al. |
| 6,325,805 B1 | 12/2001 | Oglivie et al. |
| 6,355,063 B1 | 3/2002 | Calcote |
| 6,371,990 B1 | 4/2002 | Ferree |
| 6,383,214 B1 | 5/2002 | Banas et al. |
| 6,398,803 B1 | 6/2002 | Layne et al. |
| 6,402,750 B1 | 6/2002 | Atkinson et al. |
| 6,416,537 B1 | 7/2002 | Martakos et al. |
| 6,419,704 B1 | 7/2002 | Ferree |
| 6,425,919 B1 | 7/2002 | Lambrecht et al. |
| 6,428,576 B1 | 8/2002 | Haldimann |
| 6,436,143 B1 | 8/2002 | Ross et al. |
| 6,443,988 B2 | 9/2002 | Felt et al. |
| 6,482,235 B1 | 11/2002 | Lambrecht et al. |
| 6,491,690 B1 | 12/2002 | Goble et al. |
| 6,503,269 B2 | 1/2003 | Neild et al. |
| 6,508,839 B1 | 1/2003 | Lambrecht et al. |
| 6,520,967 B1 | 2/2003 | Cauthen |
| 6,530,932 B1 | 3/2003 | Swayze et al. |
| 6,530,933 B1 | 3/2003 | Yeung et al. |
| 6,579,291 B1 | 6/2003 | Keith et al. |
| 6,592,625 B2 | 7/2003 | Cauthen |
| 6,648,915 B2 | 11/2003 | Sazy |
| 6,712,853 B2 | 3/2004 | Kuslich |
| 6,719,797 B1 | 4/2004 | Ferree |
| 6,726,696 B1 | 4/2004 | Houser et al. |
| 6,749,605 B2 | 6/2004 | Ashley et al. |
| 6,783,546 B2 | 8/2004 | Zucherman et al. |
| 6,805,695 B2 | 10/2004 | Keith et al. |
| 6,821,276 B2 | 11/2004 | Lambrecht et al. |
| 6,855,166 B2 | 2/2005 | Kohrs |
| 6,883,520 B2 | 4/2005 | Lambrecht et al. |
| 6,932,841 B2 | 8/2005 | Skylar et al. |
| 6,936,072 B2 | 8/2005 | Lambrecht et al. |
| 6,969,404 B2 | 11/2005 | Ferree |
| 7,033,393 B2 | 4/2006 | Gainer et al. |
| 7,052,516 B2 | 5/2006 | Cauthen, III et al. |
| 7,094,258 B2 | 8/2006 | Lambrecht et al. |
| 7,124,761 B2 | 10/2006 | Lambrecht et al. |
| 7,144,397 B2 | 12/2006 | Lambrecht et al. |
| 7,163,561 B2 | 1/2007 | Michelson |
| 7,198,047 B2 | 4/2007 | Lambrecht et al. |
| 7,220,281 B2 | 5/2007 | Lambrecht et al. |
| 7,223,289 B2 | 5/2007 | Trieu et al. |
| 7,258,700 B2 | 8/2007 | Lambrecht et al. |
| 2001/0004710 A1 | 6/2001 | Felt et al. |
| 2002/0007218 A1 | 1/2002 | Cauthen |
| 2002/0045942 A1 | 4/2002 | Ham |
| 2002/0049498 A1 | 4/2002 | Yuksel et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147496 A1 | 10/2002 | Belef et al. |
| 2002/0151979 A1 | 10/2002 | Lambrecht et al. |
| 2002/0151980 A1 | 10/2002 | Cauthen |
| 2002/0165542 A1 | 11/2002 | Ferree |
| 2002/0189622 A1 | 12/2002 | Cauthen, III et al. |
| 2002/0198599 A1 | 12/2002 | Haldimann |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0040796 A1 | 2/2003 | Ferree |
| 2003/0074075 A1 | 4/2003 | Thomas, Jr. et al. |

| | | | |
|---|---|---|---|
| 2003/0074076 A1 | 4/2003 | Ferree et al. | |
| 2003/0078579 A1 | 4/2003 | Ferree | |
| 2003/0093155 A1 | 5/2003 | Lambrecht et al. | |
| 2003/0125807 A1 | 7/2003 | Lambrecht et al. | |
| 2003/0130738 A1 | 7/2003 | Hovda et al. | |
| 2003/0149438 A1 | 8/2003 | Nichols et al. | |
| 2003/0158604 A1* | 8/2003 | Cauthen et al. | 623/17.16 |
| 2004/0002764 A1 | 1/2004 | Gainor et al. | |
| 2004/0010317 A1 | 1/2004 | Lambrecht et al. | |
| 2004/0024465 A1 | 2/2004 | Lambrecht et al. | |
| 2004/0030392 A1 | 2/2004 | Lambrecht et al. | |
| 2004/0034429 A1 | 2/2004 | Lambrecht et al. | |
| 2004/0044412 A1 | 3/2004 | Lambrecht et al. | |
| 2004/0097924 A1 | 5/2004 | Lambrecht et al. | |
| 2004/0116922 A1 | 6/2004 | Hovda et al. | |
| 2004/0133229 A1 | 7/2004 | Lambrecht et al. | |
| 2004/0138673 A1 | 7/2004 | Lambrecht et al. | |
| 2004/0260238 A1 | 12/2004 | Call | |
| 2004/0260300 A1 | 12/2004 | Gorensek et al. | |
| 2004/0260305 A1 | 12/2004 | Gorensek et al. | |
| 2004/0260397 A1 | 12/2004 | Lambrecht et al. | |
| 2005/0004578 A1 | 1/2005 | Lambrecht et al. | |
| 2005/0010205 A1 | 1/2005 | Hovda et al. | |
| 2005/0033440 A1 | 2/2005 | Lambrecht et al. | |
| 2005/0033441 A1 | 2/2005 | Lambrecht et al. | |
| 2005/0038519 A1 | 2/2005 | Lambrecht et al. | |
| 2005/0060038 A1 | 3/2005 | Lambrecht et al. | |
| 2005/0206039 A1 | 9/2005 | Lambrecht et al. | |
| 2005/0234557 A1 | 10/2005 | Lambrecht et al. | |
| 2005/0240269 A1 | 10/2005 | Lambrecht et al. | |
| 2006/0030857 A1 | 2/2006 | de Villiers et al. | |
| 2006/0129156 A1 | 6/2006 | Cauthen et al. | |
| 2006/0161162 A1 | 7/2006 | Lambrecht et al. | |
| 2006/0200246 A1 | 9/2006 | Lambrecht et al. | |
| 2006/0217811 A1 | 9/2006 | Lambrecht et al. | |
| 2006/0217812 A1 | 9/2006 | Lambrecht et al. | |
| 2006/0247785 A1 | 11/2006 | Gorensek et al. | |
| 2006/0253121 A1 | 11/2006 | Gorensek et al. | |
| 2006/0282167 A1 | 12/2006 | Lambrecht et al. | |
| 2007/0061012 A1 | 3/2007 | Cauthen, III | |
| 2007/0067039 A1 | 3/2007 | Lambrecht et al. | |
| 2007/0118133 A1 | 5/2007 | Lambrecht et al. | |
| 2007/0118226 A1 | 5/2007 | Lambrecht et al. | |
| 2007/0156244 A1 | 7/2007 | Cauthen | |
| 2007/0185497 A1 | 8/2007 | Cauthen et al. | |
| 2007/0260249 A1 | 11/2007 | Boyajian et al. | |

FOREIGN PATENT DOCUMENTS

| | | |
|---|---|---|
| EP | 0298235 | 1/1989 |
| EP | 0700671 A1 | 3/1996 |
| EP | 0277678 A1 | 8/1998 |
| EP | 0876808 | 11/1998 |
| EP | 0722700 B1 | 12/1998 |
| EP | 1091776 | 5/2004 |
| EP | 1214026 | 4/2005 |
| EP | 1180978 | 5/2005 |
| FR | 2639823 A1 | 6/1990 |
| JP | S63-95043 | 4/1988 |
| JP | S64-887 | 1/1989 |
| JP | H05-29694 | 2/1993 |
| RU | 2020901 | 10/1994 |
| RU | 93031998 A | 11/1995 |
| RU | 2055544 | 3/1996 |
| RU | 2078551 | 5/1997 |
| RU | 96121354 A | 1/1999 |
| WO | WO 92/10982 | 9/1992 |
| WO | WO 95-26689 | 10/1995 |
| WO | WO 95-31946 | 11/1995 |
| WO | WO 95-34331 | 12/1995 |
| WO | WO96/01164 | 1/1996 |
| WO | WO 96/01598 | 1/1996 |
| WO | WO 97-26847 | 7/1997 |
| WO | WO 97-30638 | 8/1997 |
| WO | WO 98-17190 | 4/1998 |
| WO | WO 98-20939 | 5/1998 |
| WO | WO 98-34552 | 8/1998 |
| WO | WO 98/38918 | 9/1998 |
| WO | WO 99-00074 | 1/1999 |
| WO | WO 99-02108 | 1/1999 |
| WO | WO 99-02214 | 1/1999 |
| WO | WO 99-03422 | 1/1999 |
| WO | WO 99-30651 | 6/1999 |
| WO | WO 99-47058 | 9/1999 |
| WO | WO 99-61084 | 12/1999 |
| WO | WO 99-62439 | 12/1999 |
| WO | WO 00/14708 | 3/2000 |
| WO | WO 00-18328 | 4/2000 |
| WO | WO 00-42953 | 7/2000 |
| WO | WO 00-44288 | 8/2000 |
| WO | WO 00-45741 | 8/2000 |
| WO | WO 00/49978 | 8/2000 |
| WO | WO 00-62832 | 10/2000 |
| WO | WO 00/71043 | 11/2000 |
| WO | WO 01-10316 | 2/2001 |
| WO | WO 01-12080 | 2/2001 |
| WO | WO 01/12107 | 2/2001 |
| WO | WO 01-21246 A1 | 3/2001 |
| WO | WO 01-28464 | 4/2001 |
| WO | WO 01-28468 A1 | 4/2001 |
| WO | WO 01-39696 | 6/2001 |
| WO | WO 01-45577 | 6/2001 |
| WO | WO 01/45579 | 6/2001 |
| WO | WO 01-52914 | 7/2001 |
| WO | WO 02-051622 | 7/2002 |
| WO | WO 02-058599 A2 | 8/2002 |
| WO | WO 02-067824 A2 | 9/2002 |
| WO | WO 03/039328 | 5/2003 |
| WO | WO 03/088876 | 10/2003 |

OTHER PUBLICATIONS

Bao Q.B. Bagga C.S. "The Dynamic Mechanical Analysis of Hydrogel Elastomers." Thermochimica Acta 226:107-113 (1993).

Bao Q.B. McCullen G.M. Higham P.A. Dumbleton J.H. Yuan H.A. "The Artificial Disc: Theory Design and Materials" Biomaterials vol. 17 No. 12:1157-1167 (1996).

Bao Q.B. Yuan H.A. "Artificial Disc Technology" Neurosurg Focus 9(4) 2000.

Hedman T.P. Kostuik J.P. Fernie G.R. Hellier W.G. "Design of an Intervertebral Disc Prosthesis" Spine 16 (Suppl. 6):S256-S260 (1991).

Husson J.L. Baumgartner W. Le Huec J.C. "Nucléoplastie Inter-Somatique Par Voie Postérieure Per-Dissectomie: Concept et Étude Expérimentale." Restabilisation Inter-Somatique Due Rachis Lombaire: 311-320 (1996).

Husson J.L. Scharer N. Le Nihouannen J.C. Freudiger S. Baumgartner W. Polard J.L. "Nucleoplasty During Discectomy Concept and Experimental Study." Rachis vol. 9 No. 3:145-152 (1997).

Khelimsky et al. "Plastic Surgery of Damaged Intervertebral Discs with Fast-Solidifying Glue Composition (Experimental Research)." Collected articles Experimental Traumatic Surgery and Orthopaedics Moscow 1990 pp. 88-90.

Langrana N.A. Parsons J.R. Lee C.K. Vuono-Hawkins M. Yang S.W. Alexander H. "Materials and Design Concepts for an Intervertebral Disc Spacer. I. Fiber-Reinforced Composite Design" Journal of Applied Biomaterials vol. 4:125-132 (1994).

Lemaire J.P. Skalli W. Lavaste F. Templier A. Mendes F. Diop A. Sauty V. Laloux E. "Intervertebral Disc Prosthesis." Clinical Orthopaedics and Related Research No. 337:64-76 (1997).

Martz E.O. Goel V.K. Pope M.H. Park J.B. "Materials and Design of Spinal Implants—A Review." Journal of Biomedical Materials Research vol. 38 Issue 3:267-288 (1997).

Ray C.D. Schonmayr R. Kavanagh S.A. Assell R. "Prosthetic Disc Nucleus Implants." Riv. Neuroradiol 1999:12 (Suppl. 1):157-162.

Sakalkale D.P. Bhagia S.A. Slipman C.W. "A Historical Review and Current Perspective on the Intervertebral Disc Prosthesis." Pain Physician vol. 6 No. 2:1-4 (2003).

Schonmayr R. Busch C. Lotz C. Lotz-Metz G. "Prosthetic Disc Nucleus Implants: The Wiesbaden Feasibility Study 2 Years follow-up in Ten patients" Riv. Neuroradiol 1999:12 (Suppl. 1):163-170.

Sheljakin S. Ju. "Percutaneous Diskectomy Skin-through Discectomy in Complex Treatment of Patients with Disc Lumbosacral Polyraduculitis." Abstract of a thesis St. Petersburg 1996.

Shul'man Kh.M. "Pathogenetic Therapy of Compression Type Osteochondritis of Spinal Lumbar Region." Collected articles Reconstruction-and-Restoration Treatment in Traumatic Surgery Orthopaedics Surgery and Neurosurgery Kazan' 1976 pp. 17-21.

Shul'man Kh.M. "Surgical Treatment of Compression Type Osteochondritis of Spinal Lumbar Region with Intervertebral Disc Implantation." Kazan' 1980 pp. 174-185.

Shul'man Kh.M. Danilov V.I. "Biochemical Experimental Basis of Inteverterbral Disc Prosthesis Implantation Method by Fast-solidifying Polyurethane CKYu-PFL in Case of Disc Degeneration or Traumatic Damage." Collected articles Reconstruction-Restoration Treatment in Traumatic Surgery Orthopaedics Surgery and Neurosurgery. Kazan' 1976 pp. 22-27.

Usmanov M.M. "Intervertebral Disc Changes at Local Damage of its Elements and Implantation of Various Materials." Abstract of a thesis Moscow 1991.

USSR Author's Certificate No. 1477390 "Method for Treatment of Osteochondritis." Published May 17, 1989.

USSR Author's Certificate No. 1827204 "Method for Treatment of Spinal Osteochondritis." Published May 15, 1993.

Zelentsov E.V. "Plastic Surgery with Collagen of Intervertebral Discs for Surgical Treatment of Lumbosacral Polyradiculitis." Abstract of a thesis Leningrad 1990.

Zelentsov E.V. et al. "Application of Collagen for Experimental Plastic Surgery of Intervertebral Discs." Collected articles Integrated Treating of Pain Syndromes of Neurogenic Origin Leningrad 1984 pp. 86-90.

Ahlgren, B.D., et al., "Anular Incision Technique on the Strength and Multidirectional Flexibility of the Healing Intervertebral Disc," *Spine*, 19 (8): 948-954 (1994).

Balderston, R.A., et al., "The Treatment of Lumbar Disc Herniation: Simple Fragment Excision Versus Disc Space Curettage," *J. of Spinal Disorders*, 4 (1): 22-25 (1991).

Barr, J.S., "Ruptured Intervertebral Disc and Sciatic Pain," *J. of Bone and Joint Surgery*, 29, (2): 429-437 (1947).

Brinckmann, P., et al., "Change of Disc Height, Radial Disc Bulge, and Intradiscal Pressure From Discectomy An in Vitro Investigation on Human Lumbar Discs," *Spine*, 16 (6): 641-646 (1991).

Goel, V.K., et al., "Mechanical Properties of Lumbar Spinal Motion Segments as Affected by Partial Disc Removal," *Spine*, 11 (10): 1008-1012 (1986).

Hanley, E.N., Jr., et al., "The Development of Low-Back Pain After Excision of a Lumbar Disc," *J. of Bone and Joint Surgery*, 71A (5): 719-721 (1989).

Heggeness, M.H., et al., "Discography of Lumbar Discs After Surgical Treatment for Disc Herniation," *Spine*, 22 (14): 1606-1609 (1997).

Kayama, S., et al., "Incision of the Anulus Fibrosus Induces Nerve Root Morphologic, Vascular, and Functional Changes," *Spine*, 21 (22): 2539-2543 (1996).

Postacchini, F., "Spine Update results of Surgery Compared With Conservative Management for Lumbar Disc Herniations," *Spine*, 21 (11): 1383-1387 (1996).

Rogers, L.A., "Experience with Limited versus Extensive Disc Removal in Patients Undergoing Microsurgical Operations for Ruptured Lumbar Discs," *Neurosurgery*, 22 (1): 82-85 (1988).

Tibrewal, S.B., et al., "Lumbar Intervertebral Disc Heights in Normal Subjects and Patients with Disc Herniation," *Spine*, 10 (5): 452-454 (1985).

Tullberg, T., et al., "Radiographic Changes After Lumbar Discectomy," *Spine*, 18 (7): 843-850 (1993).

Yasargil, M.G., "Microsurgical Operation of Herniated Lumbar Disc," p. 81, Adv Neurosurg (1977).

* cited by examiner

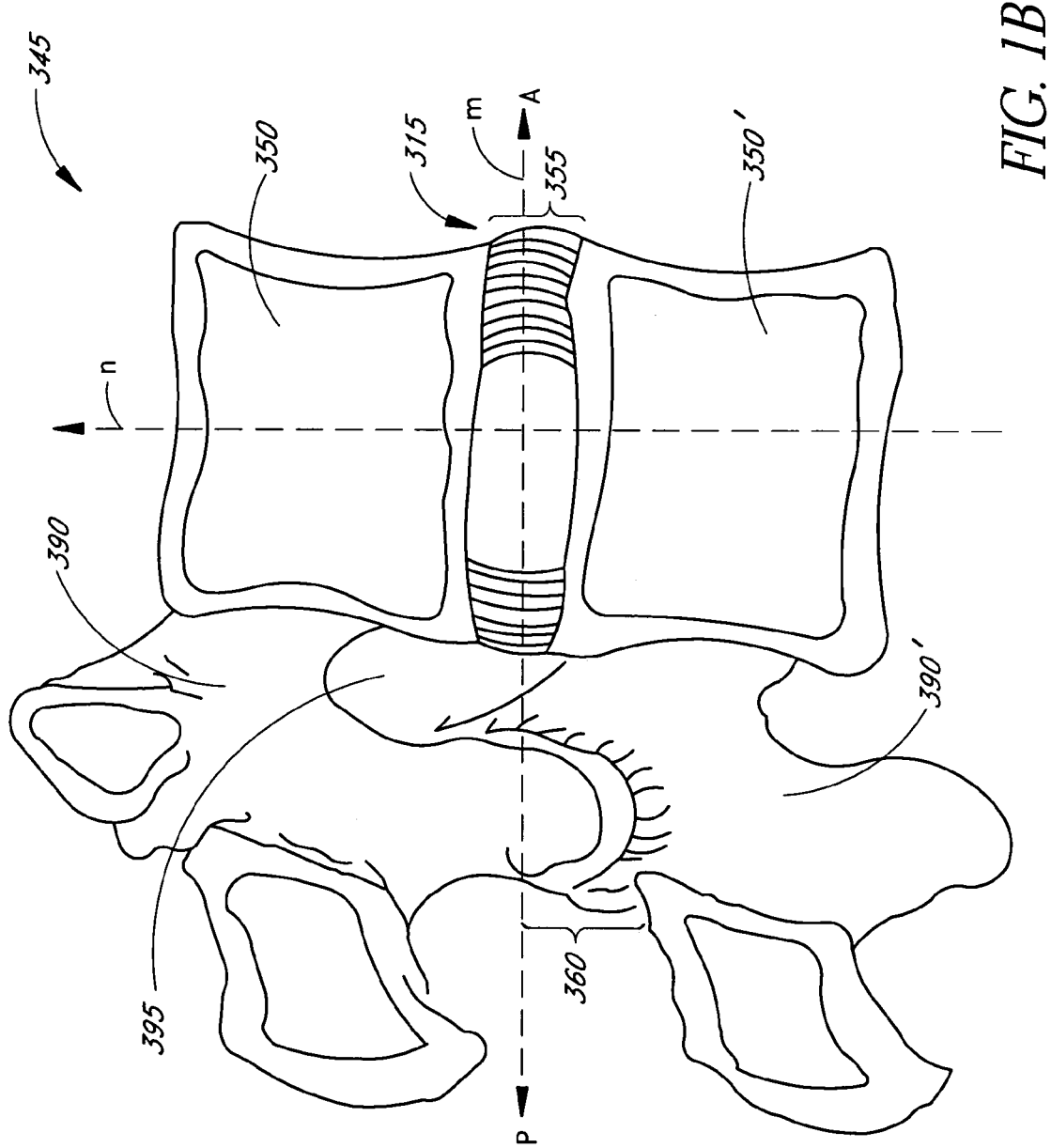

METHOD FOR DELIVERING AND POSITIONING IMPLANTS IN THE INTERVERTEBRAL DISC ENVIRONMENT

RELATED APPLICATIONS

This application is a continuation of co-pending U.S. application Ser. No. 10/873,074, filed Jun. 21, 2004, which claims priority under 35 U.S.C. §119(e) to U.S. Provisional Appl. No. 60/480,276, filed Jun. 20, 2003, herein incorporated by reference.

BACKGROUND OF THE INVENTION

1. Field of the Invention

The present invention relates generally to devices and methods for delivering implants to an intervertebral disc. Specifically, in some embodiments, apparatus and methods for delivering implants that are oriented and compressed for minimally invasive, yet precise and effective implantation are provided.

2. Description of the Related Art

Various implants, surgical meshes, patches, barriers, tissue scaffolds and the like may be used to treat intervertebral discs and are known in the art. Surgical repair meshes are used throughout the body to treat and repair damaged tissue structures such as intralinguinal hernias, herniated discs and to close iatrogenic holes and incisions as may occur elsewhere. Certain physiological environments present challenges to precise and minimally invasive delivery.

An intervertebral disc provides a dynamic environment that produces high loads and pressures. Typically, implants designed for this environment, unless used for temporary purposes, must be capable of enduring such conditions for long periods of time. Also, the difficulty and danger of the implantation procedure itself, due to the proximity of the spinal cord, limits the size and ease of placement of the implant. In light of the inherent limitations involved with delivery of medical devices to the disc environment, such devices should preferably be delivered precisely with respect to the location of the defect.

SUMMARY OF THE INVENTION

In one embodiment of the present invention, devices and methods for delivering implants to an intervertebral disc are provided. In a preferred embodiment, delivery methods are designed to prevent or reduce exacerbation of the existing defect or iatrogenic hole. One of skill in the art will understand that several embodiments of the invention can be used to deliver implants, or other medical devices, to sites in the body other than the intervertebral disc. For example, several embodiments of the invention can be used to deliver medical devices (such as implants) into the heart, bladder, liver, cranium, vertebrae, femur and other bones In one embodiment, a method of delivering and positioning a medical device (such as an implant) within an intervertebral disc is provided. In one embodiment, the method comprises providing a cannula, an advancer, one or more expanders and an implant. The advancer is at least partially coupled to, slideably engaged to, or housed within the cannula. The advancer is coupled to an implant, or is operable to be coupled to an implant. The implant is operable to exhibit a compressed profile along one or more axes. The method further comprises compressing the implant along a first axis, and inserting the cannula into a interverterbral disc. The method further comprises positioning the cannula in the disc such that the implant is positioned beyond the innermost surface of the anulus, rotating the cannula or advancer, retracting the cannula, thereby initially expanding the implant, advancing one or more expanders, thereby further expanding the implant, advancing the cannula, thereby substantially completely expanding the implant, uncoupling the implant from the advancer, and removing the cannula and the advancer from the disc. In one embodiment, the cannula or advancer is rotated clockwise or counterclockwise to enable the implant to be rotate in a range from about 80 degrees to about 120 degrees. Preferably the implant is rotated about 90 degrees. In other embodiments, the above steps are performed using a medical device other than an implant. In some embodiments, the medical device (such as an implant) is delivered to a site other than the disc. These sites include, but are not limited to, the heart, cranium or femur. In one embodiment, one or more depth stops are coupled to the cannula, advancer, or delivered as a separate component. In one embodiment, when the cannula is inserted into the disc, the depth stop is placed at a position adjacent an external surface of an intervertebral disc and the implant is delivered relative to that position.

In one embodiment, the step of compressing the implant comprises folding the implant. In other embodiments, compressing the implant comprises folding, deflating, compacting, compressing, closing or condensing the implant, or a combination thereof.

In one embodiment, the step of expanding the implant comprises unfolding the implant. In other embodiments, expanding the implant comprises unfolding, inflating, enlarging, swelling, or opening the implant, or a combination thereof.

In one embodiment, the implant is a barrier or patch. Implants suitable for implantation according to one or more embodiments of the invention include the implants described in U.S. Pat. Nos. 6,425,919, 6,482,235, and 6,508,839, all herein incorporated by reference.

In a further embodiments, one or more implants are inserted through a defect or iatrogenic hole.

In one embodiment, a method of delivering a medical device (such as an implant) within an intervertebral disc is provided. In one embodiment, the method comprises providing an implant that is capable of exhibiting a compressed profile along one or more axes, compressing the implant along a first axis, inserting the implant within an intervertebral disc along a second axis and beyond the innermost lamella of an anulus lamella, rotating the implant about an axis perpendicular to the second axis; and causing or allowing the implant to transform from a compressed profile to an expanded profile.

In another embodiment, a method of delivering a medical device (such as an implant) within an intervertebral disc comprises providing a delivery device having an elongate implant advancer carried within or alongside an elongate sleeve. In one embodiment, the advancer is releaseably coupled to an implant, wherein the implant is compressed within the sleeve at a distal end of the sleeve. The method further comprises advancing the distal end of the sleeve with an intervertebral disc along a first axis, rotating the advancer, releasing the implant from the sleeve thereby decompressing the implant, and releasing the implant from the advancer.

In a further embodiment, a method of delivering a medical device (such as an implant) in an intervertebral disc wherein the disc has a defect or iatrogenic hole forming a void in the anulus of the disc is provided. In one embodiment, the method comprises providing a compressible implant having a first and second axis, compressing an implant along a first axis, orienting the implant to such that the short axis of the compressed implant presents a profile the is smaller than the largest dimension of the void, inserting the implant beyond the defect or iatrogenic hole, rotating the implant clockwise or counterclockwise about ninety degrees, causing or allowing the implant to expand or unfold, and retracting at least a portion of the implant against an inner surface of the anulus.

In yet another embodiment, a method of delivering a medical device (such as an implant) in an intervertebral disc along an innermost surface of an anulus of the disc is provided. In one embodiment, the method comprises inserting the implant through and beyond the innermost surface of the anulus, retracting the implant toward the innermost surface of the anulus, and deflecting at least a portion of the implant against the innermost surface of the anulus, thereby causing the implant to advance laterally along said surface.

In yet another embodiment, a method of delivering a medical device (such as an implant) in an intervertebral disc along an innermost surface of an anulus of the disc is provided. In one embodiment, the method comprises inserting the implant within the disc and beyond the innermost surface of the anulus, retracting the implant toward the innermost surface of the anulus, and deflecting at least a portion of the implant against the innermost surface of the anulus, thereby causing the implant to advance laterally along said surface. In one embodiment, the implant is expanded. In some embodiments, the method further comprises simultaneously retracting and deflecting the implant. In sever embodiments, the method further comprises simultaneously retracting and deflecting the implant in a synchronized manner. In a preferred embodiment, the method comprises rotating the implant.

In one embodiment of the invention, a device for delivering and positioning an implant within an intervertebral disc is provided. In one embodiment, the device comprises a cannula and an advancer. In one embodiment, the cannula has a proximal end and a distal end, wherein the distal end comprises one or more expanders operable to expand an implant positioned beyond the innermost lamella of a disc anulus. In one embodiment, the advancer has a proximal end and a distal end, wherein the advancer is positioned at least partially within the cannula. The distal end of the advancer comprises a coupling mechanism, wherein the coupling mechanism is coupled to the advancer and to the implant. In another embodiment, the expanders are not located on the cannula, but instead coupled to the advancer. In one embodiment, the expanders are located on a separate instrument. In one embodiment, the device comprises one or more depth stops. The depth stop can be coupled to any portion of the cannula or advancer, or can be independently delivered. In one embodiment, the depth stop is operable to limit and/or guide travel within the intervertebral disc. In a further embodiment, the depth stop is rotatably coupled to the cannula, thereby allowing it to rotate while the depth of the cannula is maintained.

In one embodiment, the advancer is advanced through a sheath or other constraining means, and no cannula is used. In another embodiment, the advancer is coupled to a constraining means at its distal end that is operable to constrain the implant until the implant reaches the desired site (such as a site located beyond the innermost lamella of the anulus)

BRIEF DESCRIPTION OF THE DRAWINGS

FIGS. 1A-1C show disc anatomy. FIGS. 1A and 1B show the general anatomy of a functional spinal unit. FIG. 1A is a view of a transverse section of a functional spinal unit. FIG. 1B is a view of a sagittal section. FIG. 1C shows the same functional spine unit with a defect in the anulus, which may have been created iatrogenically, as in the performance of an anulotomy, or may be naturally occurring.

FIG. 3A is an isometric view of another delivery device in accordance with an embodiment of the present invention. FIG. 3B is an isometric view of the above delivery device loaded with an implant folded in place at the slotted distal end of the cannula. FIG. 3C is an isometric view of the above delivery device loaded with an implant in an unfolded configuration. FIG. 3D is an isometric partial view of the distal end of a delivery device loaded with a folded implant. FIG. 3E is a cross-sectional partial view of the distal end of an unloaded delivery device showing the implant coupling member.

FIG. 4A is a side view of a functional spinal unit showing a defect in the posterior anulus of the disc. FIG. 4B is a side view of a functional spinal unit showing a delivery device inserted within the disc.

FIG. 5A is an axial view of the cross-section of an intervertebral disc with a delivery device inserted within the disc.

FIG. 7A shows an implant compressible along two axes which can be used with various embodiments of the invention. FIG. 7B is a top view (as it would be viewed along the superior-inferior axis of a vertebral in its implanted orientation) of an implant and lateral extensions or stabilizers. FIG. 7C shows the same implant folded or compressed in an accordion like manner to facilitate loading into the cannula. FIG. 7D is an isometric view of another implant suitable for use with some embodiments of the invention having a concavity along its length and extensions.

DETAILED DESCRIPTION OF THE PREFERRED EMBODIMENT

Several embodiments of the invention will be discussed herein through the demonstration of its use in the spine, with particular emphasis on intervertebral disc treatment. One of skill in the art will certain understand that several embodiments of the invention can be used to access or treat other sites in the body.

Figure 1A:
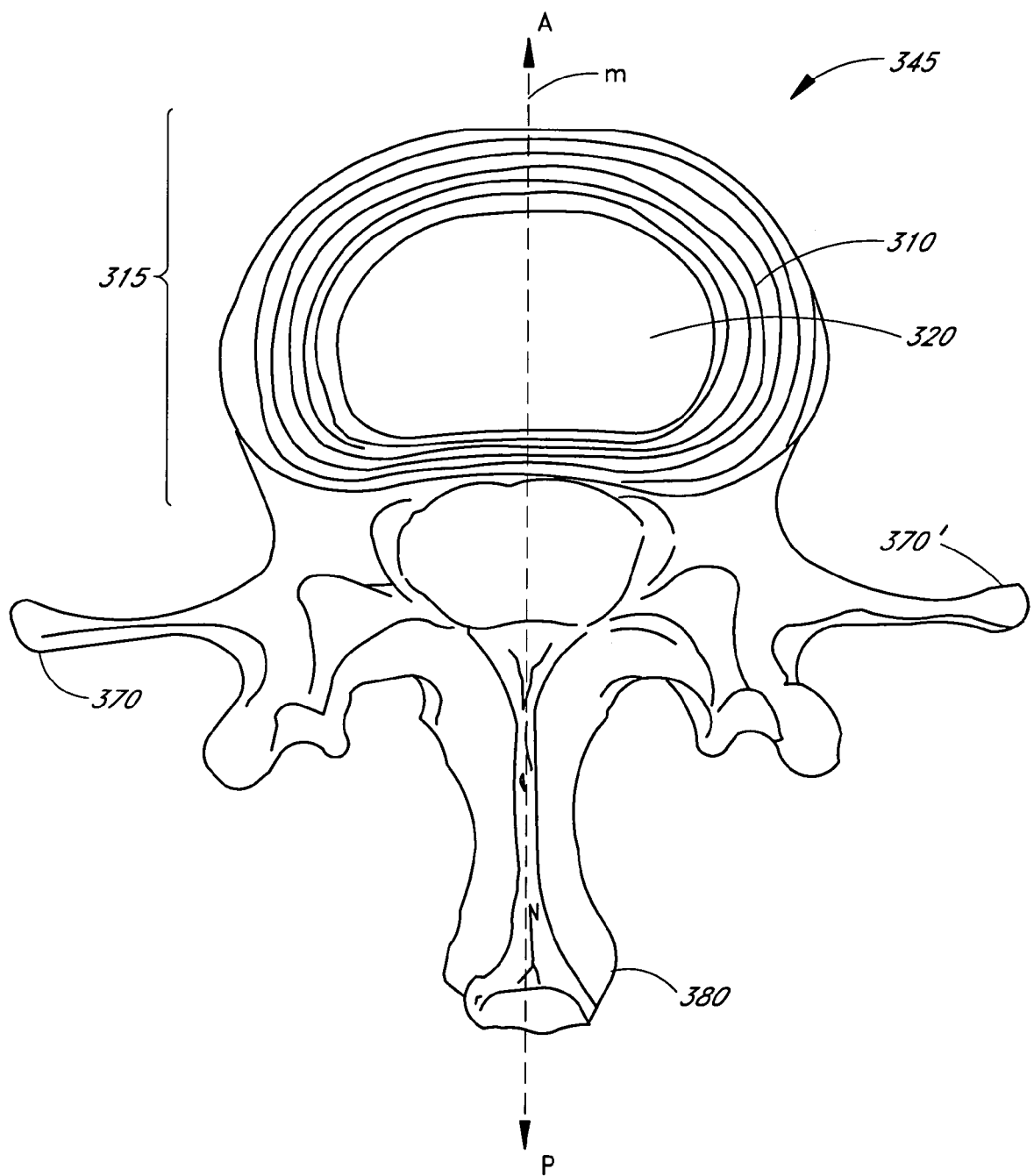

FIGS. 1A and 1B show the general anatomy of a functional spine unit. In this description and the following claims, the terms 'anterior' and 'posterior', 'superior' and 'inferior' are defined by their standard usage in anatomy, e.g., anterior is a direction toward the front (ventral) side of the body or organ, posterior is a direction toward the back (dorsal) side of the body or organ; superior is upward (toward the head) and inferior is lower (toward the feet).

FIG. 1A is an axial view along the transverse axis M of a vertebral body with the intervertebral disc 315 superior to the vertebral body. Axis M shows the anterior (A) and posterior (P) orientation of the functional spine unit within the anatomy. The intervertebral disc 315 contains the anulus fibrosus (AF) 310 which surrounds a central nucleus pulposus (NP) 320. Also shown in this figure are the left 370 and right 370' transverse spinous processes and the posterior spinous process 380.

FIG. 1B is a sagittal section along sagittal axis N through the midline of two adjacent vertebral bodies 350 (superior)

and 350' (inferior). Intervertebral disc space 355 is formed between the two vertebral bodies and contains intervertebral disc 315, which supports and cushions the vertebral bodies and permits movement of the two vertebral bodies with respect to each other and other adjacent functional spine units.

Intervertebral disc 315 is comprised of the outer AF 310, which normally surrounds and constrains the NP 320 to be wholly within the borders of the intervertebral disc space. Axis M extends between the anterior (A) and posterior (P) of the functional spine unit. The vertebrae also include facet joints 360 and the superior 390 and inferior 390' pedicle that form the neural foramen 395. The facet joints and intervertebral disc translate motion and transfer load between the adjacent vertebral bodies. This complex biomechanical arrangement allows for flexion, extension, lateral bending, compression, and can withstand intense axial loading and bending cycles of around a million per year. The disc height can vary from 50% to 200% of its resting value.

Figure 1C:
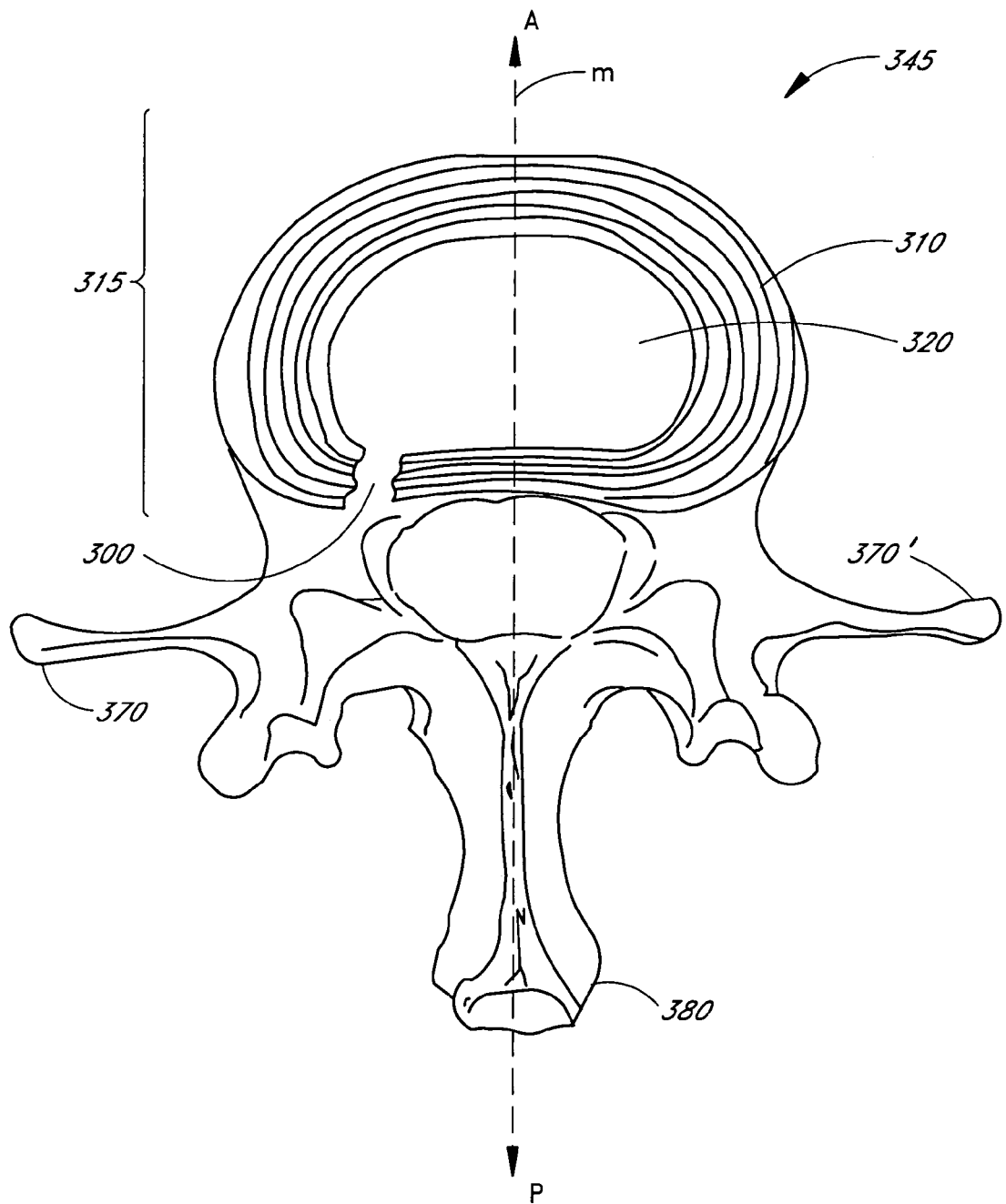
Figure 2A:
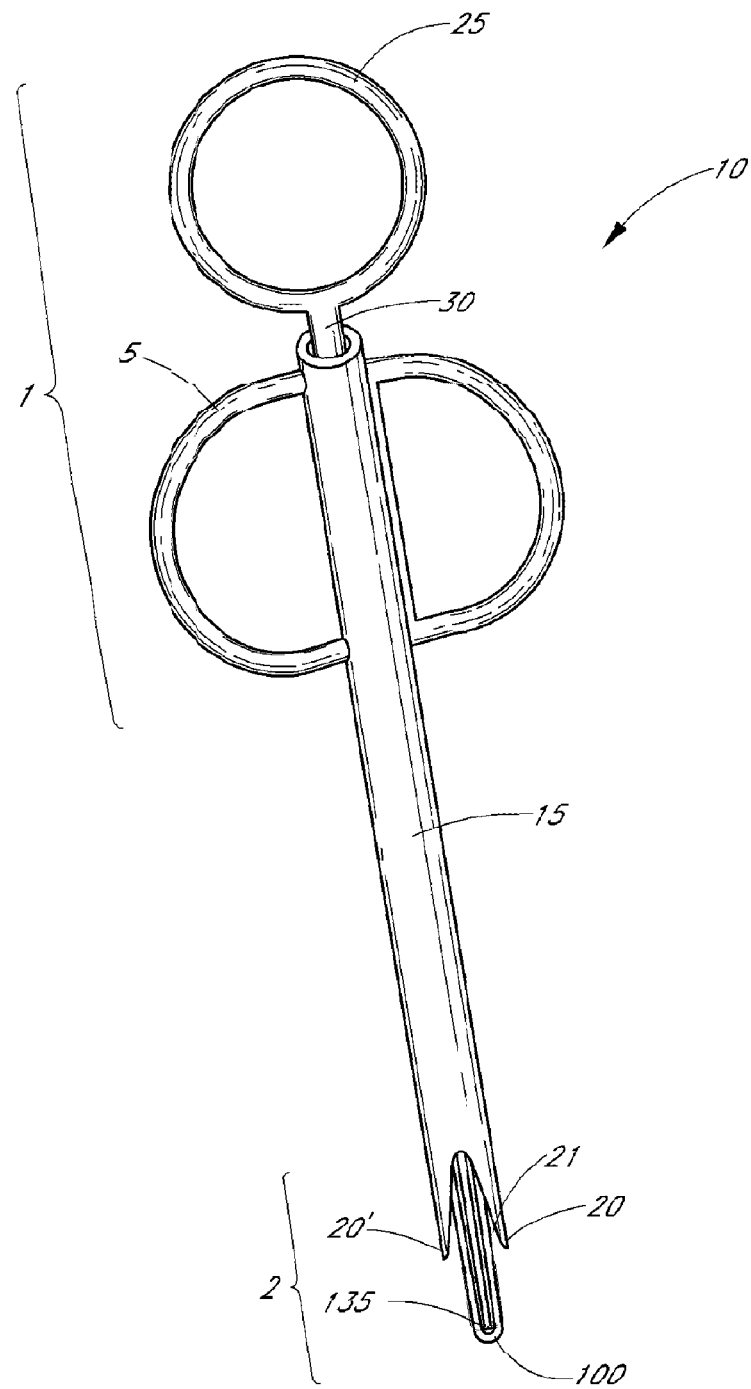
FIGS. 2A-2D are front views of a delivery device and its elements in accordance with an embodiment of the present invention.
Figure 2B:
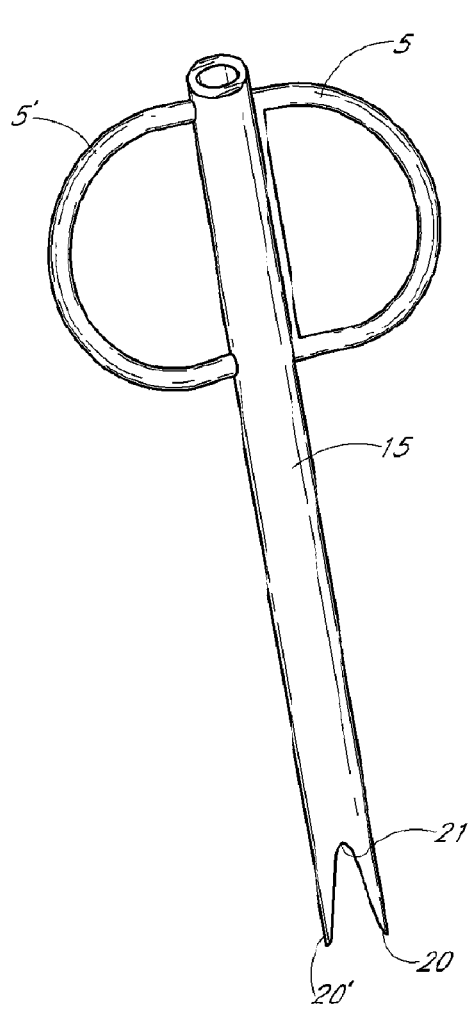
Figure 2C:
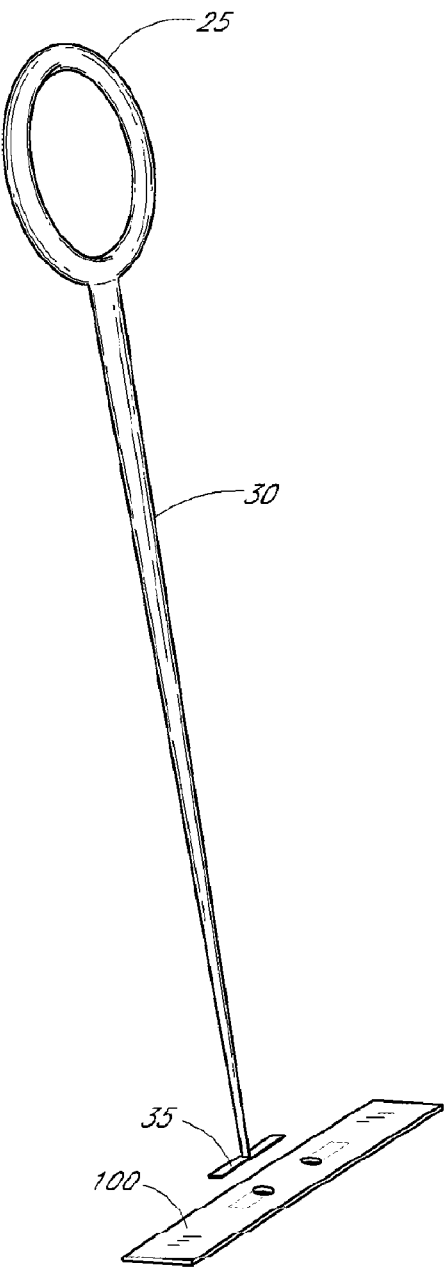
Figure 2D:
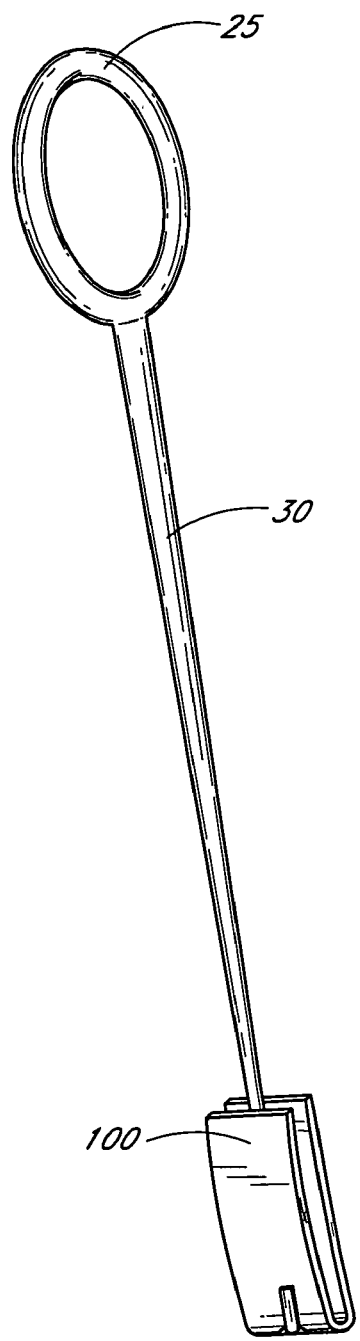

FIG. 1C shows the same functional spine unit with a defect in the anulus, which may have been created iatrogenically, as in the performance of an anulotomy, or may be naturally occurring. Such a defect can be repaired, in one embodiment, using a surgical mesh or therapeutic mesh, or the like. In one embodiment, the mesh can be impregnated or coated with therapeutic agents or drugs to regrow or otherwise stimulate healing or growth or ingrowth as described herein.

In one embodiment of the invention, a method and device capable of delivering a therapeutic implant in a minimally invasive manner is provided. In a preferred embodiment, delivery provides accurate and precise placement of the implant, while still being minimally invasive. In one embodiment, the implant is placed along a tissue surface in an expanded or manipulated configuration and orientation that differs from the insertion configuration and orientation.

In several embodiments, methods and apparatuses for delivering surgical meshes, barriers, patches, or the like, for treatment or augmentation of tissues within pathologic spinal discs and other structures are provided. In one embodiment, a dynamic and synergistic delivery method and device that allow for an integrated re-orientation, expansion and delivery of an implant in a confined and limiting environment is provided.

According to one embodiment, an instrument designed to assist in the delivery and positioning of a implant within or adjacent to the various tissues generic to intervertebral disc, including the vertebral bodies and their endplates, the anulus fibrosis, the nucleus pulposus, and the surrounding ligaments, is provided.

One advantage of several embodiments of the invention are particularly advantageous because, in some indications, a practitioner has to deliver an implant or other medical device that has a complicated configuration. For example, some implants have one or more dimensions in their implanted or deployed state that make it difficult or impossible to insert due, for example, to physiological size or geometrical constraints. Such implants may have a second dimension which is also larger than the allowed dimensions available for insertion. For example, the height of the implant may be greater than the height of the opening or anulotomy or the height of the space between the adjacent endplates at their periphery. Further, the length of some implants may also be larger than the width anulotomy.

In one embodiment, an instrument and method that can effectively deliver medical devices to a desired site is provided. The method is particularly advantageous for delivering medical devices having challenging configurations. In one embodiment, the method comprises first inserting the implant rotated relative to the limiting dimension to achieve a diminished or compatible profile and then rotating the implant back to the desired orientation and expanded during final positioning. In a preferred embodiment, this method is accomplished using a single instrument. Other embodiments comprise using two or more compatible instruments.

In one embodiment of the invention, a delivery device comprising a cannula, a proximal end and a distal end is provided. In one embodiment, the elongated, hollow cannula or sleeve has a proximal end for handling by a physician and a distal end for inserting within a patient is provided. The distal end of the cannula can be dimensioned to fit within a small anulotomy as might be created by a surgeon or through a naturally occurring hole or lesion in the anulus.

In a further embodiment, an implant guide or advancer is carried within the cannula or sleeve. In one embodiment, the guide or advancer is releaseably coupled to an implant that may be compressed within the cannula along one or more axes. In one embodiment, the guide or advancer is axially moveable within the cannula and can rotate depending on the implant used or implantation site selected. The cannula functions as a guide for the axial reciprocal movement the advancer. As such, in one embodiment, the cannula can, therefore, be provided in the form of an elongate tube having a central lumen for receiving advancer therethrough. Alternatively, the cannula can comprise a nontubular structure or simply a sleeve or partial restraining member in an embodiment in which the advancer travels concentrically over or alongside it.

In one embodiment, a substantially rectangular implant is provided. In several embodiments, the implant is a mesh comprised of nitinol, steel, or polymer, or a combination thereof. In other embodiment, the implant comprises a seeded or unseeded tissue scaffold, such as collagen or small intestine sub mucosa, and the like.

In one embodiment, the implant can be folded across its long axis, connected to the advancer, and inserted within the sleeve at the distal end of the delivery device. If the fold created along the short axis is larger that the sleeve diameter then one or more slots can be formed at the tip of the sleeve to accept the implant. Alternatively, the implant can be compressed along the second or short axis of the implant so that both dimensions are held compressed within the sleeve. One of skill in the art will understand the implant, if needed, can be compressed along any axis in accordance with several embodiments of the invention. Compressing the implant (or medical device), as used herein, shall be given its ordinary meaning and shall also include folding, deflating, compacting, compressing and condensing the implant or medical device.

In one embodiment, in use, the distal end of the sleeve is inserted into the desired organ or tissue structure, such as an intervertebral disc. The implant is loaded into the sleeve such that the fold is at or near the distal end of the sleeve. Depending on the shape of the insertion site (e.g., a rectangular anulotomy), and its orientation (vertical or horizontal), the implant or advancer can be rotated in order to pass through the aperture regardless of the desired implantation orientation. Accordingly, devices according to one or more embodiments of the invention can cause the implant to rotate between around 5 and 150 degrees and preferably between around 60 and 120 degrees. In one embodiment, at least a portion of the delivery device is rotated clockwise or counterclockwise in the range of between about 2 to 170 degrees, preferably between about 50 to 140 degrees, more preferably about 80 to 120 degrees, thereby enabling rotation of the implant. In one embodiment, the device or the implant is rotated about 90 degrees.

In one embodiment, as the sleeve loaded with the compressed implant is inserted medially into the disc, the surgeon may stop inserting when the edges of the folded-over implant pass beyond the corresponding tissue surface against which implantation is desired. In this example, the surgeon would stop after passing the anulus or the outer and more narrow gap between the periphery of the adjacent vertebral endplates. Thereafter, the implant can be rotated about an axis perpendicular to the insertion axis to correspond to the desired insertion orientation. Next, the sleeve is retracted relative to the advancer to reveal the folded (and now unrestrained or actively compressed) implant. Depending on the orientation of the implant within the sleeve (after the rotation step), the implant will expand inferiorly and superiorly with respect to the endplates or laterally to the left and right along the anulus. In one embodiment, as the implant unfolds due to its inherent resilience, or by a force imparted by the coupling member or cannula, or by active manipulation by the physician, the advancer is then retracted such that the folded part of the implant is pulled posteriorly in the direction of the posterior anulus and the sides or extensions of the implant advance laterally or travel along the anulus surface. When the action of the advancer causes the implant to be fully retracted flat along the tissue surface or is otherwise in its fully expanded position then the surgeon may detach the implant from the advancer.

One of ordinary skill in the art will understand the kinematics, order, relative position, and orientation of the implant, sleeve, and advancer can be reversed or altered to achieve similar or equivalent results for a given implantation according to several embodiments to the invention. For example, in one embodiment, the advancer can be used to extrude the implant out from the sleeve. In another embodiment, the sleeve can be retracted relative to the advancer. In a further embodiment, the advancer can be retracted to pull the implant posteriorly and along the posterior anulus or alternatively, the whole device (including the sleeve or cannula and advancer) can be pulled back. Both the advancer and the sleeve independently or the device itself can be used to rotate the implant. In one embodiment, at least a potion of the device remains stationary while one or more of its elements are manipulated. In another embodiment the delivery device is simplified with the use of a constraining member used in place of the sleeve to hold the implant in a compressed state at the distal end of the advancer. For example a suture, clamp, ring, band, pincher, or an adhesive could be used to constrain the implant and then the advancer could still server to advance the implant within the disc and rotate it into position.

In several embodiments, parts of the device can serve different purposes during steps of the implantation. In one embodiment, the sleeve can constrain and then release the folded or compressed implant and later, when the implant is released and in a slightly expanded state (larger that the profile of the cannula opening or tip), the cannula can be advanced (or the advancer can be retracted) such that the cannula or sleeve tip contacts the inside surface of the folded sides of the implant and forces them to open. Accordingly, in one embodiment, the retracting step involving posterior movement of the midsection of the implant and lateral movement of the sides of the implant along the anulus surface caused by the opposing force of the anulus causing lateral deflection may be unnecessary since the opposing and synchronized action and relative motion of the advancer and cannula tip effectively act like a lever and fulcrum to open, expand or unfold the implant. In one embodiment, the connector at the fold or hinge of the implant acts like a fulcrum and the distal tips of the cannula act like levers to push the fold flat and open the implant. This alternative or complimentary step or method of opening may be particularly useful in expanding the implant proximal to a large defect of weakened portion of the anulus since such tissue might not offer a solid deflection surface for the opposing ends of the implant to advance along.

FIGS. 2A-2D show one embodiment of the invention. A delivery device 10 is shown having an elongate cannula having a proximal end 1 and distal end 2. The cannula 15 has a distal end tip 20 or ends 20, 20' formed by a slot 21 cut into its distal end 2 for accepting and constraining a compressed implant 100. Also shown are the cannula finger handles 5, 5', advancer 30, advancer ring handle 25 at the proximal end 1 and implant/advancer coupling member 35 at the distal end 2 of the device.

In one embodiment, a coupling member 35 is used. The coupling member 35 is any device or mechanism that is capable of attaching or connecting the implant in reversible manner. Coupling members include, but are not limited to, sutures, snaps, locks, lynch pins or the like, levers and slots, or any active or passive linking mechanism known in the art that would permit a surgeon to disengage the implant at the desired point of the procedure. In one embodiment, one or more coupling members are used. In one embodiment, two coupling members are used to connect the implant.

In one embodiment, the device 10 is designed to be operated by one hand, e.g., utilizing the thumb, index, and ring fingers to position the device 10 and advance and retract the advancer 30. However, one skilled in the art will understand that any of a variety of proximal handpieces can alternatively be used, including, but not limited to, triggers, slider switches, rotatable knobs or other actuators to advance and retract the advancer 30.

In one embodiment, the delivery device 10 can be manufactured in accordance with any of a variety of techniques well known in the medical device arts. In one embodiment, the cannula 10 comprises a metal tube such as stainless steel or other medical grade metal. Alternatively, the device 10 can comprise a polymeric extrusion, such as high density polyethylene, PTFE, PEEK, PEBAX, or others well known in the medical device arts.

In a preferred embodiment, the axial length of the delivery device 10 is sufficient to reach the desired treatment site from a percutaneous or small incision access through the skin. In one embodiment, the length of the delivery device 10 is within the range of about 10 centimeters to about 30 centimeters with a length from a proximal end to distal end within the range of about 10 to about 20 centimeters contemplated for most posterior lateral access pathways. The length can be varied depending upon the intended access pathway and patient size.

In one embodiment, the outside diameter of the delivery device 10, and the distal end of the cannula 30, is no greater than necessary to accomplish the intended functions disclosed herein. In one embodiment, outside diameters of less than about one centimeter are preferred. In preferred embodiments of the present invention, the cannula 30 has an outside diameter of no greater than approximately 5 millimeters.

Figure 3A:
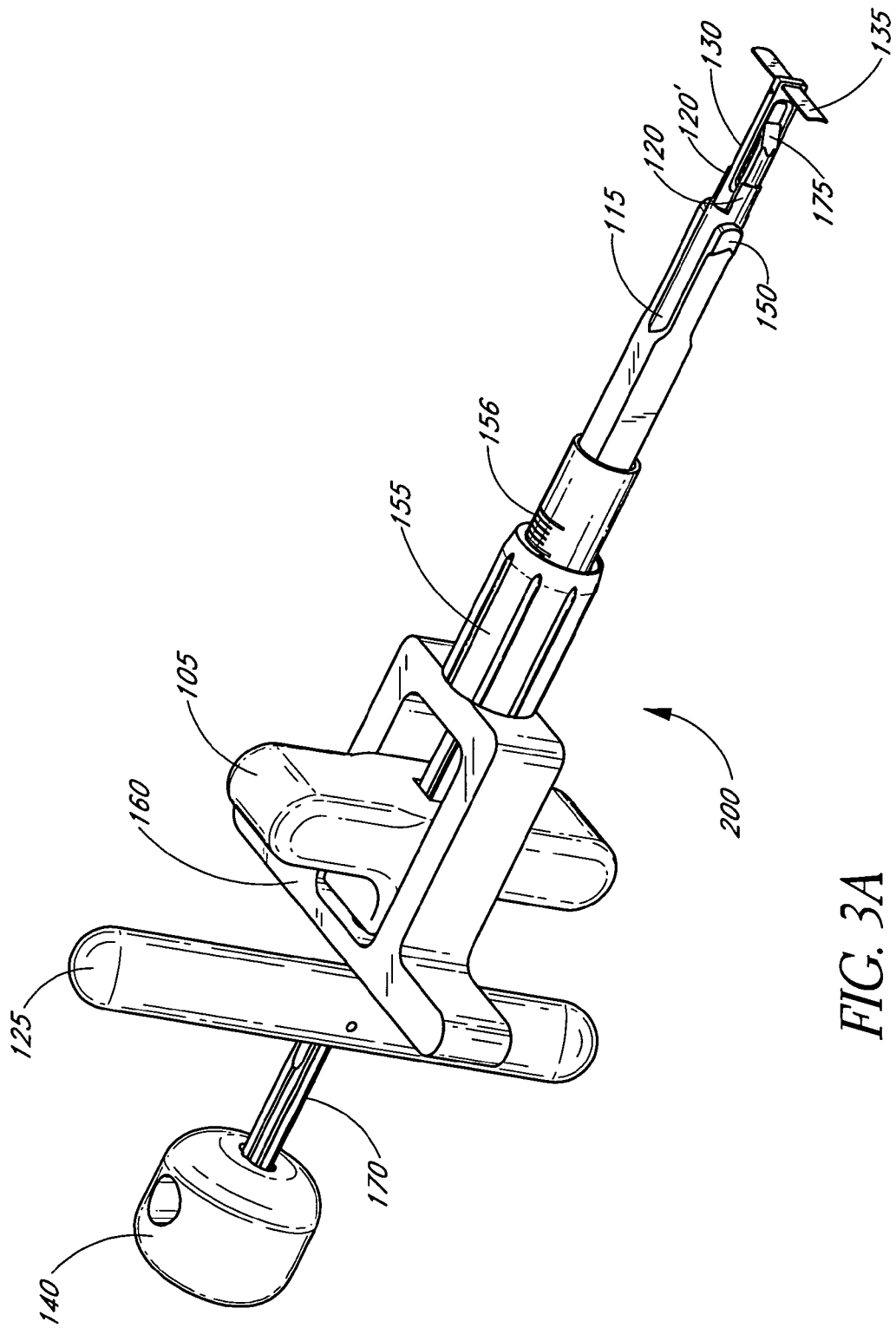
FIGS. 3A-3E show embodiments of a delivery device.

An exemplary embodiment having additional features is presented in FIGS. 3A-3E. FIG. 3A is an isometric view of an implant delivery device 200 having a proximal end 1 for manipulating by a surgeon and a distal end for inserting with a patient. In one embodiment, an implant advancer or guide 130 having a handle 125 located at the proximal end 1 of the device 200 and an implant coupling member 135 extending to the distal end 2 of the device 200 is provided. The advancer 130 is slideably housed within a cannula 115 which has a cannula handle 105 for positioning and controlling the cannula.

The device, in one embodiment, also includes a distal depth stop 150 feature that provides a limit and guide to the anterior/posterior positioning of the implant during implantation and in the final positioning of the implant. The depth stop 150 and 150' is carried by the cannula 115 and can be adjusted to rest along certain points of its length by manipulating the depth stop adjustment member 155 and holding the depth stop handle 160. A calibrated measuring surface 156 can be etched onto to the cannula or attached separately to the cannula as a sleeve to display depth correlations. Alternatively, non adjustable depth stops in a variety of lengths can be included as a kit and the precise depth stop for a given procedure can be selected preoperatively. In one embodiment, the depth stop 150 can be coupled to the cannula such that free rotation of the cannula 115 and advancer 130 are possible while maintaining the desired depth of the distal tip of the device.

In a further embodiment, to assist opening or expanding the implant, an implant expander 170 having a wedge surface(s) 175, 175' at its distal end an expander handle 140 attached at its proximal end is carried within the cannula 115 and over or along each side of the advancer 130. One or more expanders can be coupled to the cannula or the advancer. In one embodiment, a separate instrument comprising one or more expanders at its distal end is passed through the cannula.

Figure 3B:
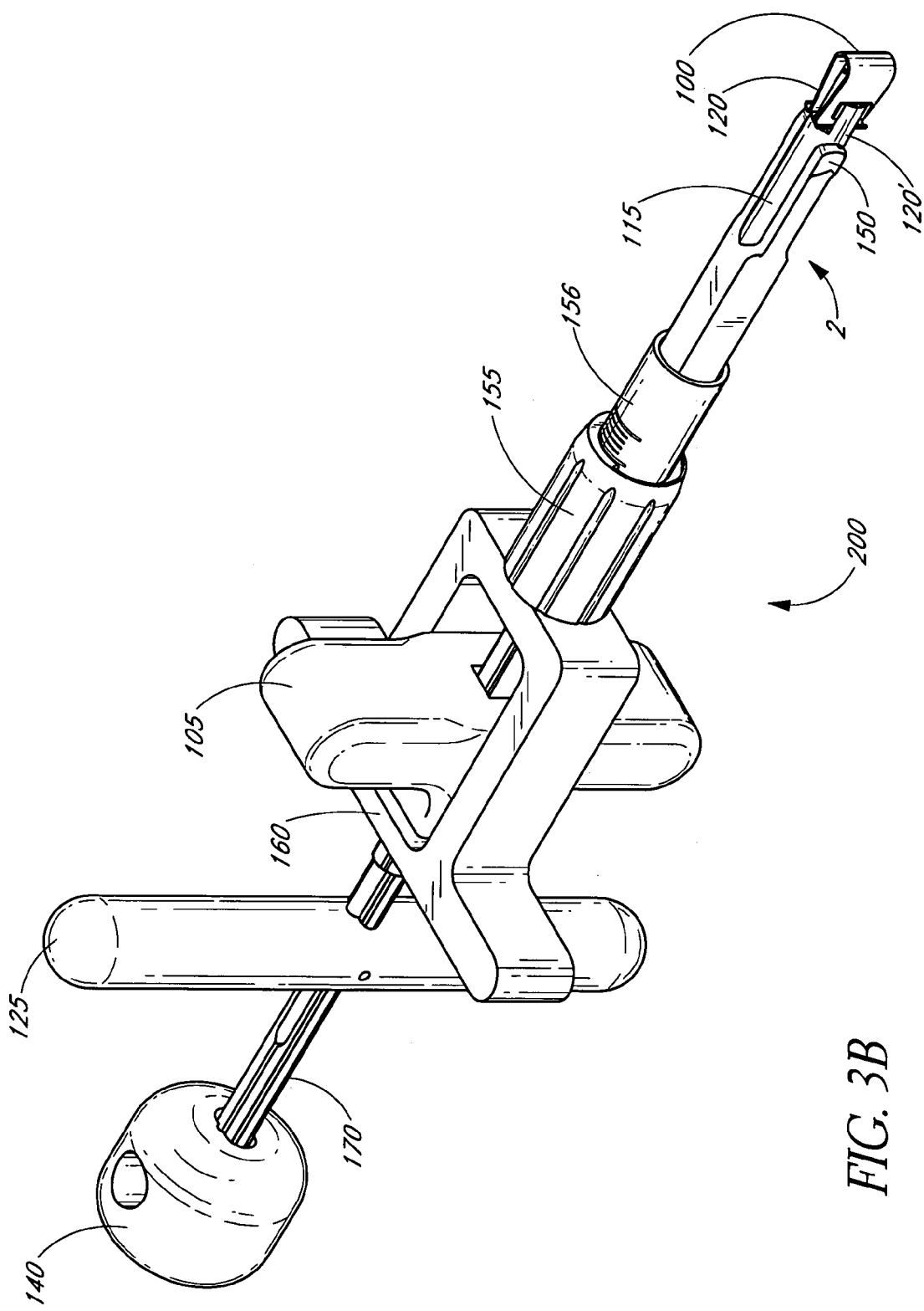
Figure 3C:
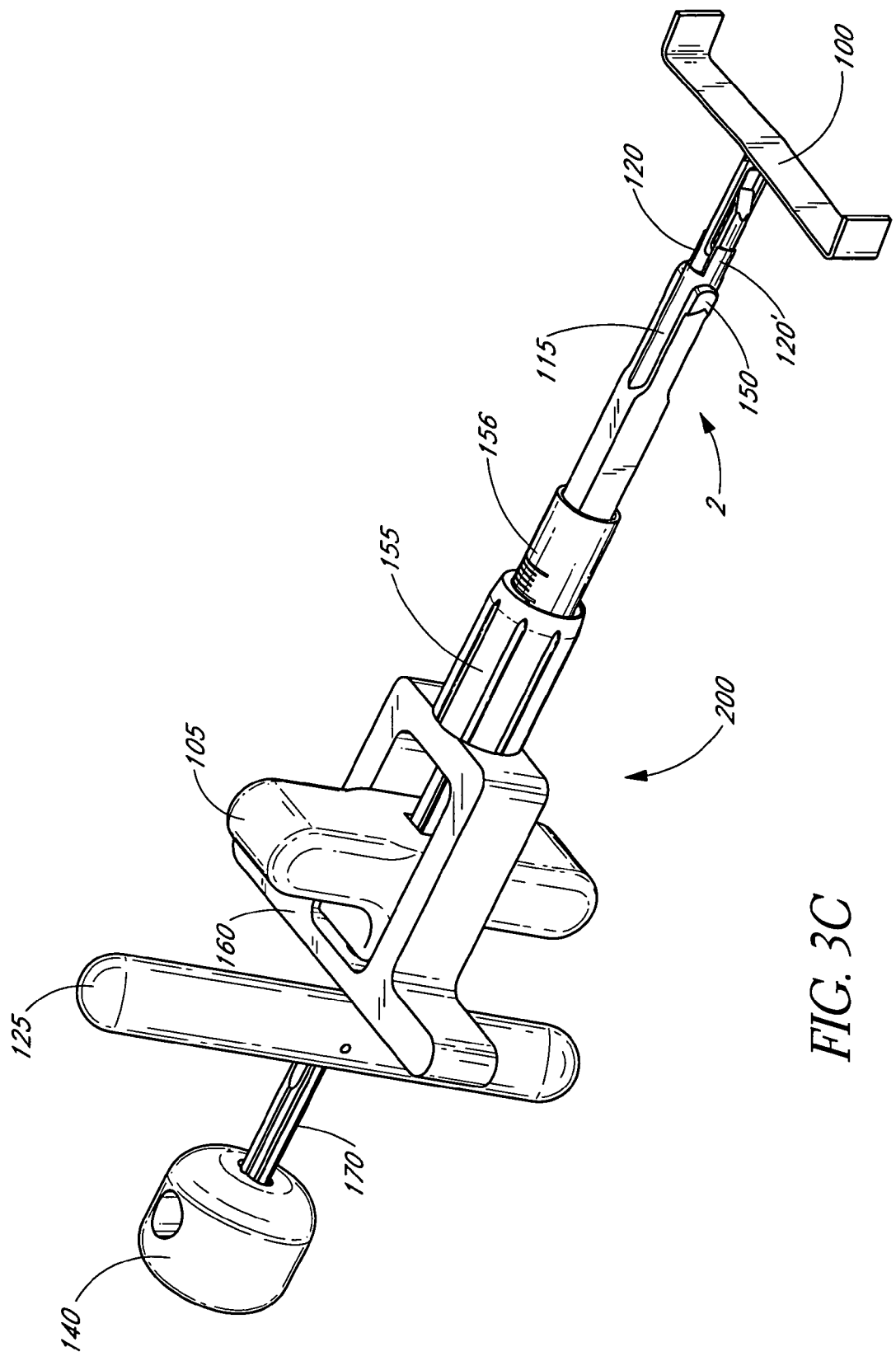

In FIG. 3B, a delivery device according to one embodiment of the invention is shown loaded with a compressed implant 100 at the distal end 2 of the device 200. As shown, in one embodiment, the rectangular implant 100 is folded over itself across its longs axis and fitted within a slot of the cannula formed by the slotted ends of the cannula 120 and 120'. In an alternative embodiment, the cannula could be straight (e.g., no slot formation) and the implant could also be compressed along its second or short axis. FIG. 3C shows the device coupled to an expanded or unfolded implant 100.

Figure 3D:
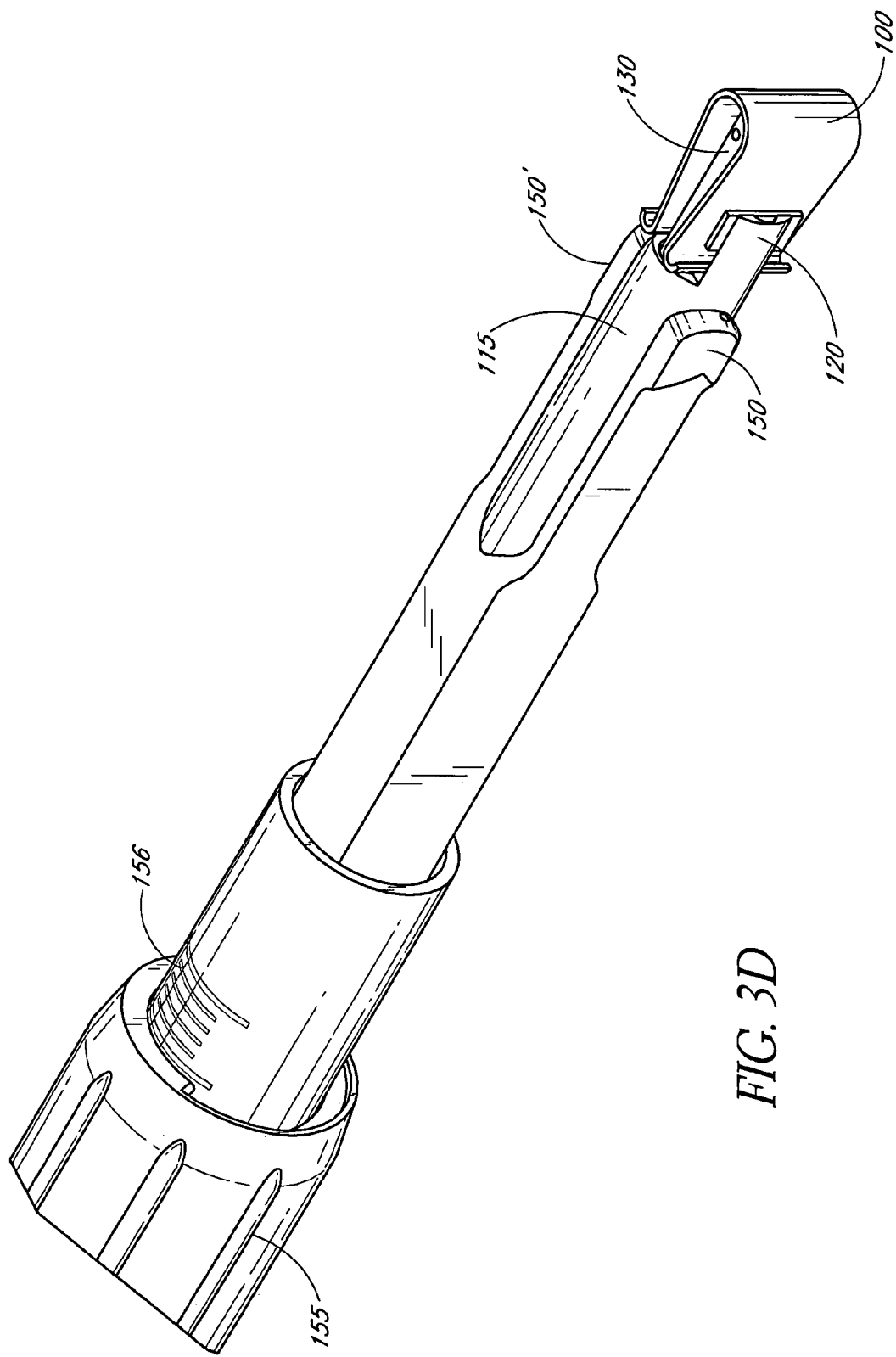

FIG. 3D shows an enlarged isometric view of the distal end of the device 200 loaded with an implant 100 between slotted end tips or tongs 120, 120' of the cannula 115. The opposing distal ends of the depth stop 150, 150' are shown as forked protrusions adjacent the cannula 115. In one embodiment, two depth stops are provided. In another embodiment, one or more depth stops are provided. In an alternative embodiment, an entire circumferential stop surface can be used.

Figure 3E:
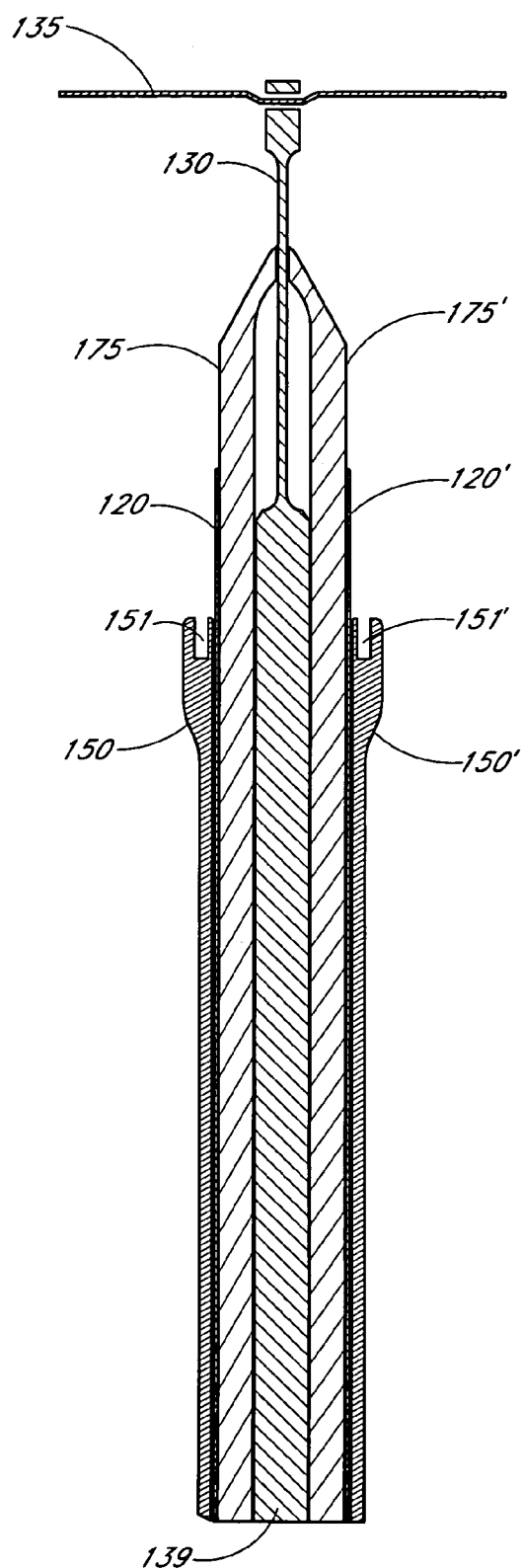

FIG. 3E shows the cross-section of the distal end of the device 200 including the expanders 175, 175' and implant/advancer coupling member 135. In one embodiment, the coupling member is a flexible "T-bar" attached lengthwise to the advancer 130 and fits into slots in the implant surface (not shown). Alternatively, active and passive coupling means described above can also be used. In one embodiment, when the expanded implant is retracted against the tip of the cannula 120 and/or the anulus surface (which is shown oversized in comparison to the mouth of the cannula or insertion site), further retraction of the advancer or the device its causes the coupling member to slip out of the slots (not shown) in the implant. Also shown are radio opaque indicators 150, 150' coupled to the depth stop 150, 150' which can be used in determining device placement during radiographic imaging. For example, portions of the device can be aligned with anatomical structures or the handles or other projections of the device can be oriented to correspond to the implants orientation. One or more radio opaque markers can be used in one embodiment of the invention. One of skill in the art will understand that other indicators or markers can also be used.

Figure 4A:
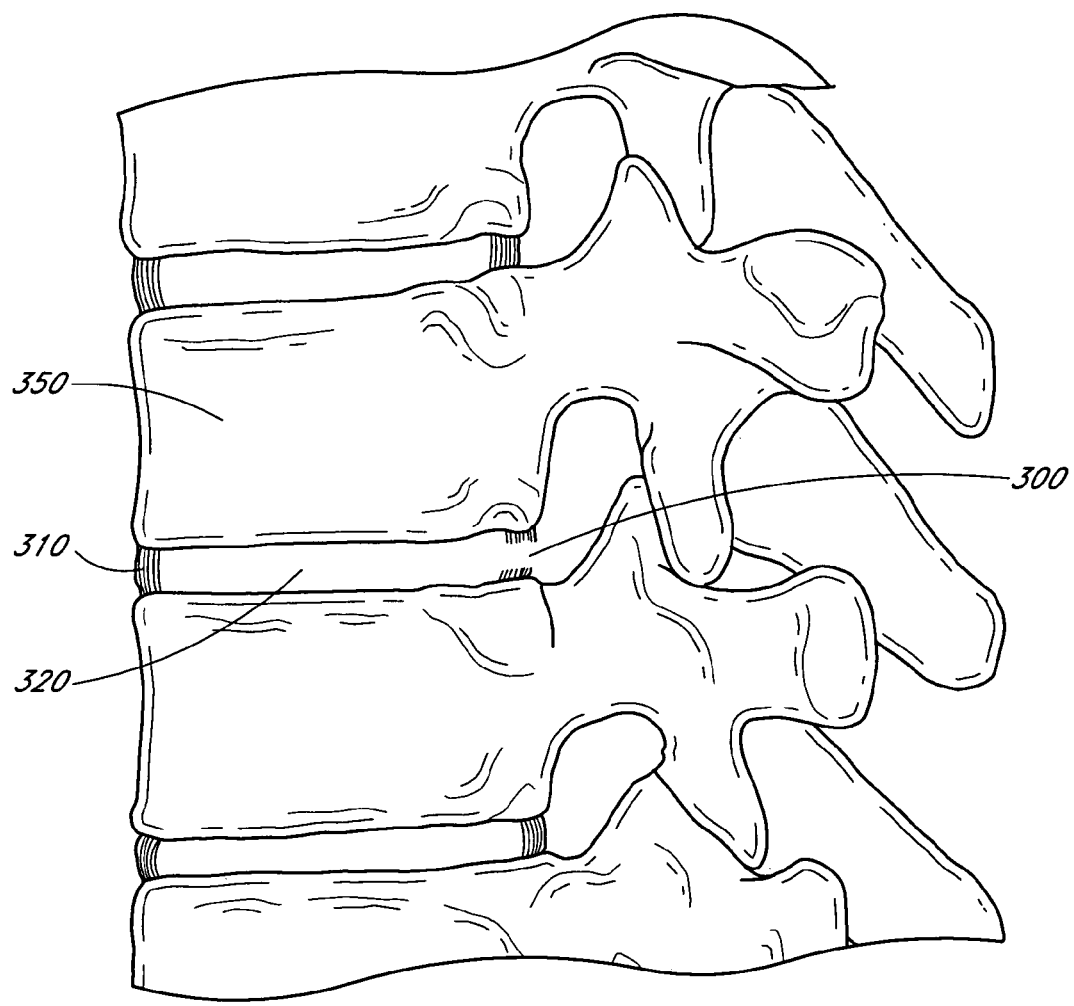
FIGS. 4A-4B show aspects of the disc.
Figure 4B:
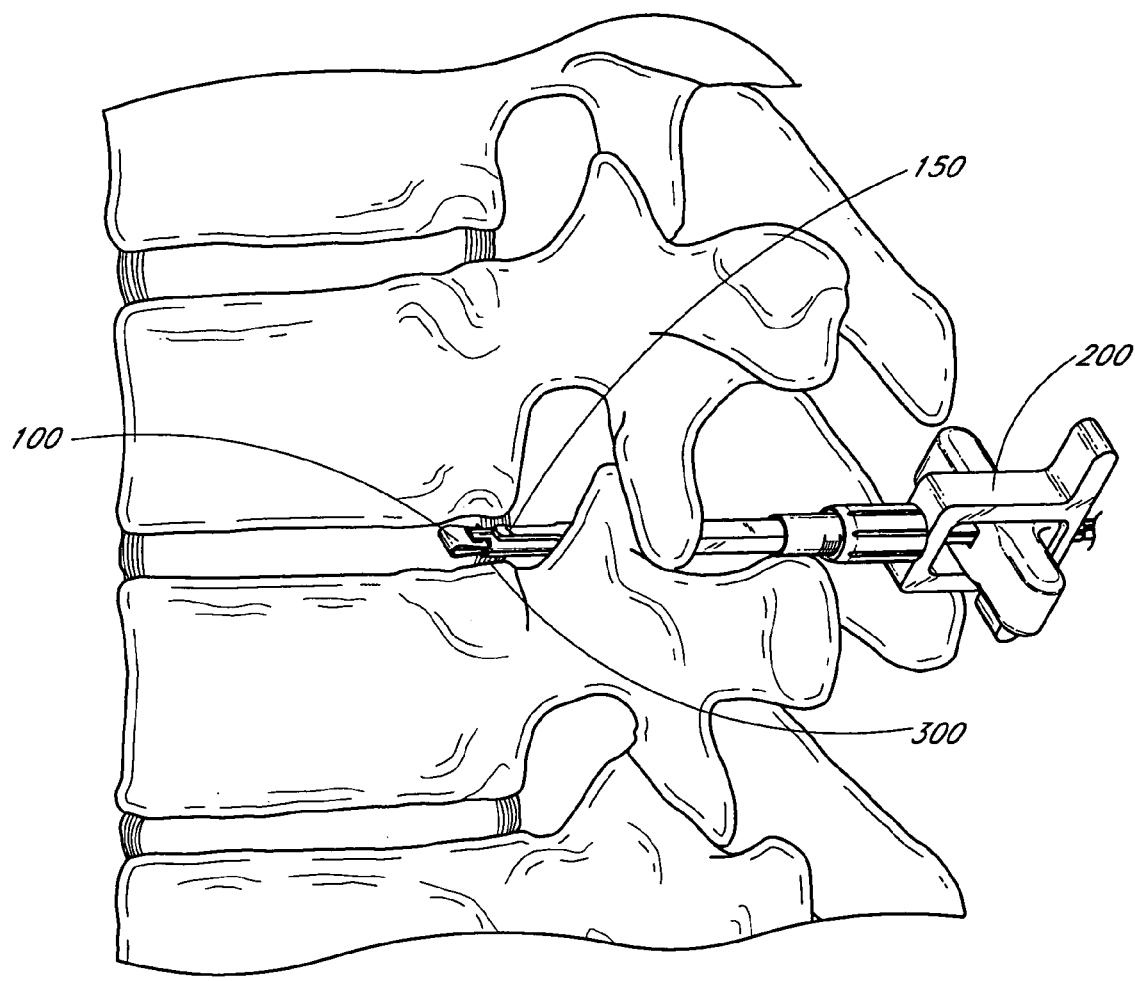

Turning to FIGS. 4A and 4B, a side view of a functional spinal unit is shown with a defect 300 in the anulus 310 (see e.g., FIGS. 1A-1C for vertebral anatomy) and the device 200 inserted in the defect. In one embodiment, a posterior lateral approach that can involve a laminotomy or modification of the posterior elements of the adjacent vertebral bodies is used. In a further embodiment, other approaches can be used, including, but not limited to, anterior (e.g., through the abdomen or neck), lateral (e.g., transpsoas), or inferior (e.g., transsacral) approaches.

The series presented in FIGS. 5A through 5G depict a sequence for delivering a generally elongate rectangular mesh implant according to an embodiment of the method. The defect 300 or box or slit anulotomy is rectangular in shape having a lateral (or width) dimension greater than its vertical dimension. Moreover, the vertical dimension may also be limited by the relative location of the endplates at the time of procedure limiting the height of a deliverable implant. In one embodiment, the implant 200 is oversized to cover the defect 300 and to function as a barrier situated against the anulus 310 along its innermost lamella.

Figure 5A:
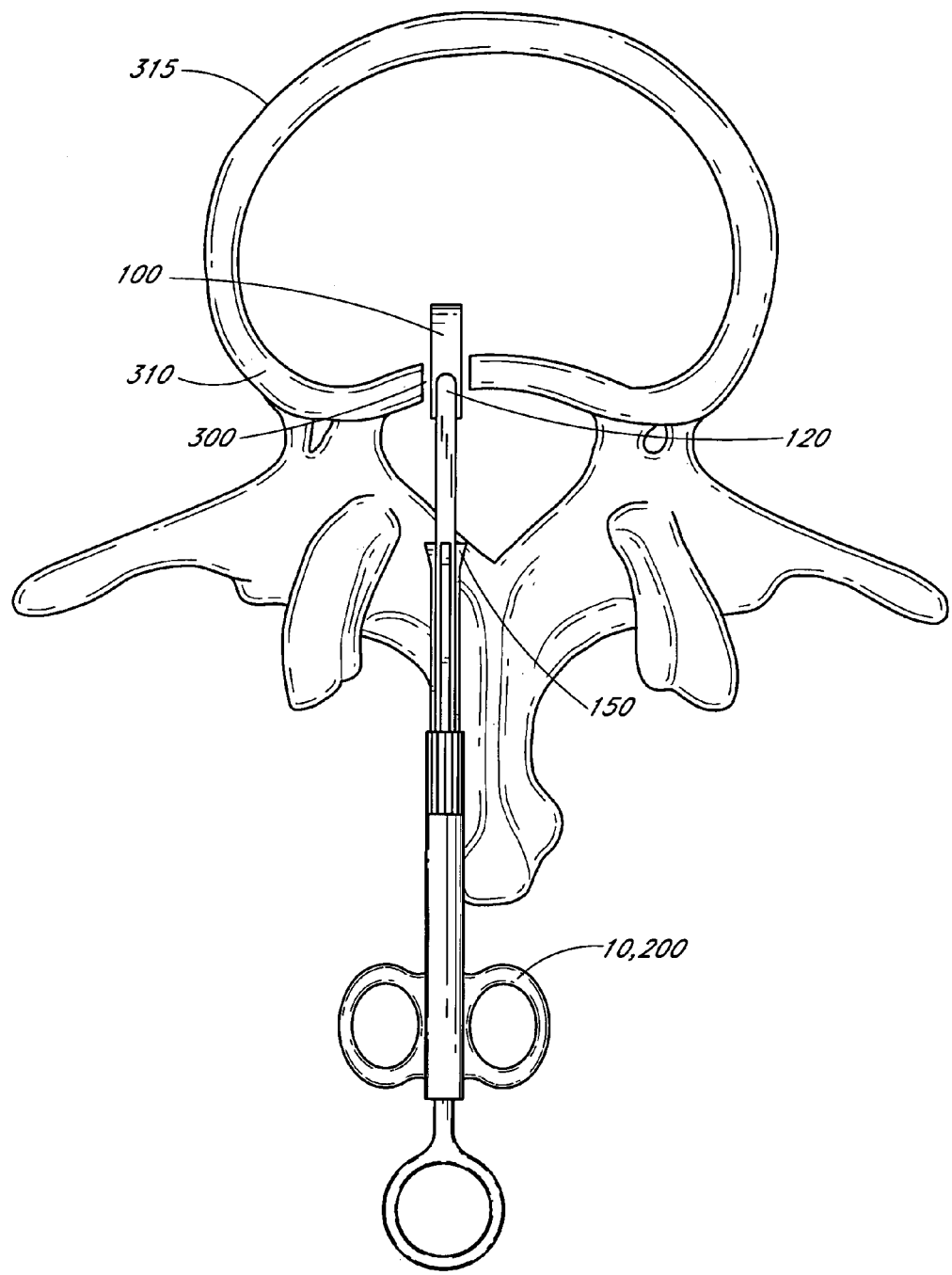
FIGS. 5A-5G illustrate one method of delivering an implant according to one embodiment of the invention.
Figure 5B:
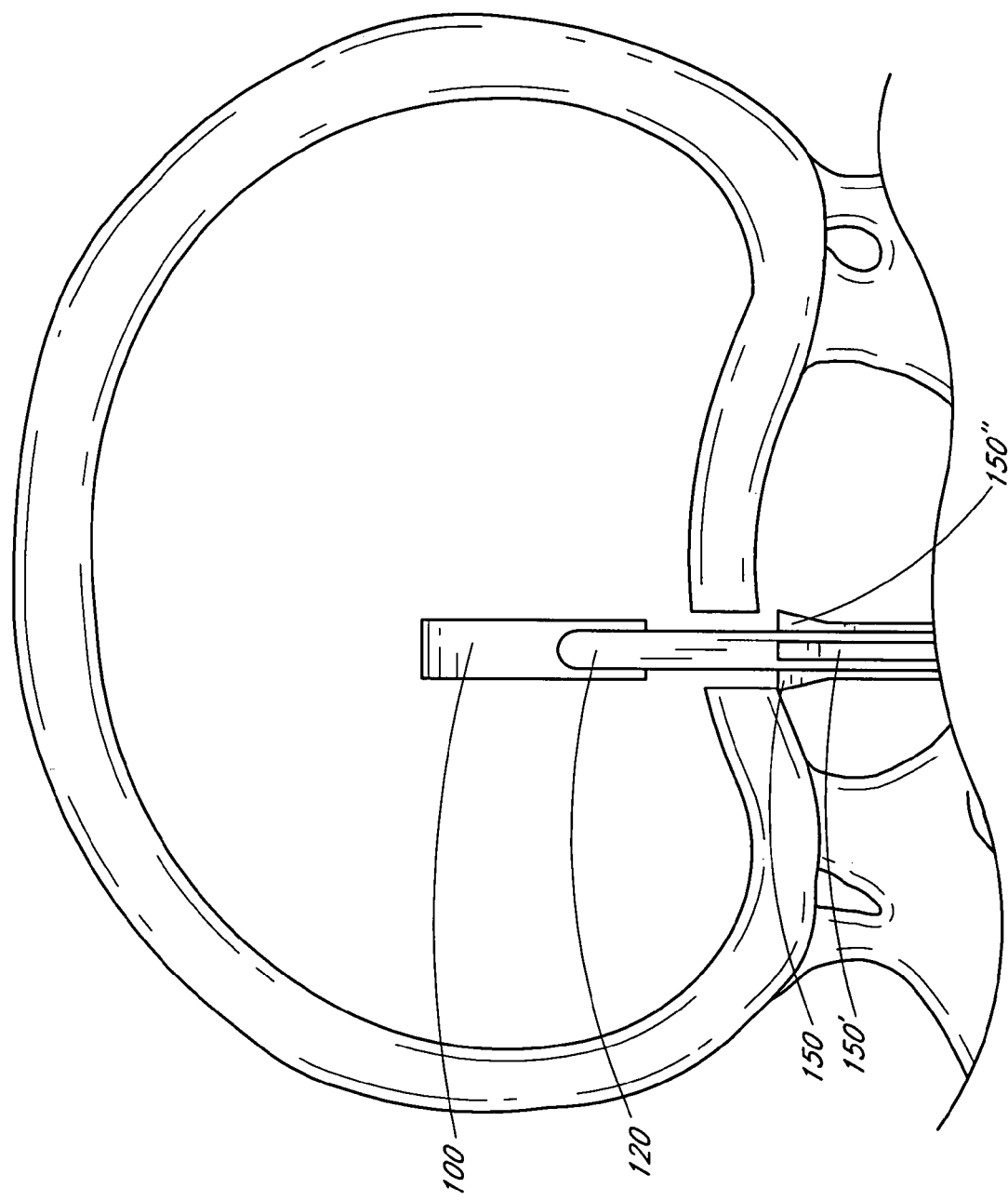

FIG. 5A is an axial view of a cross-section of the disc showing the implant 100 folded along its long axis and connected to the advancer 130 (not shown) and inserted within the distal end tips or tongs 120 of the cannula 115. Here, the fold created along the short axis is larger that the cannula 115 diameter so a slot is formed at the tip of the cannula 115 formed by opposing tips 120, (120' not shown). This arrangement permits the distal end of the device 2 loaded with the implant to be advanced within and then beyond the defect 300 and the anulus 310 as shown in FIG. 5B. Here the depth stop 150, 150', 150" is shown as three protrusions though more or less can be used. In this delivery application, portions of the depth stop 150 can be placed against the anulus or one or both of the adjacent vertebral bodies. In other embodiments, the depth stop 150 can be placed on, abut or engage the exterior of an organ, such as the heart, a bone such as cranium, femur, or vertebral body. In one embodiment, the implant is designed to have a preferred region of final placement in terms of its positioning toward the anterior or posterior of the disc (anterior being defined as the direction toward the front of the patient and posterior being defined as the direction toward the back of the patient) in front of the defect. The surgeon may also want to place the implant and have the delivery device provide a limit or guide to the distance toward the anterior of the disc in order to prevent damage to the anterior anulus or damage to anatomy anterior of the disc such as the aorta. Similarly, the surgeon may want to place the implant in a position that is not too far posterior within the disc to prevent damage to the posterior anulus or anatomy posterior to the disc such as the spinal cord and its dura mater or the posterior longitudinal ligament.

Figure 5C:
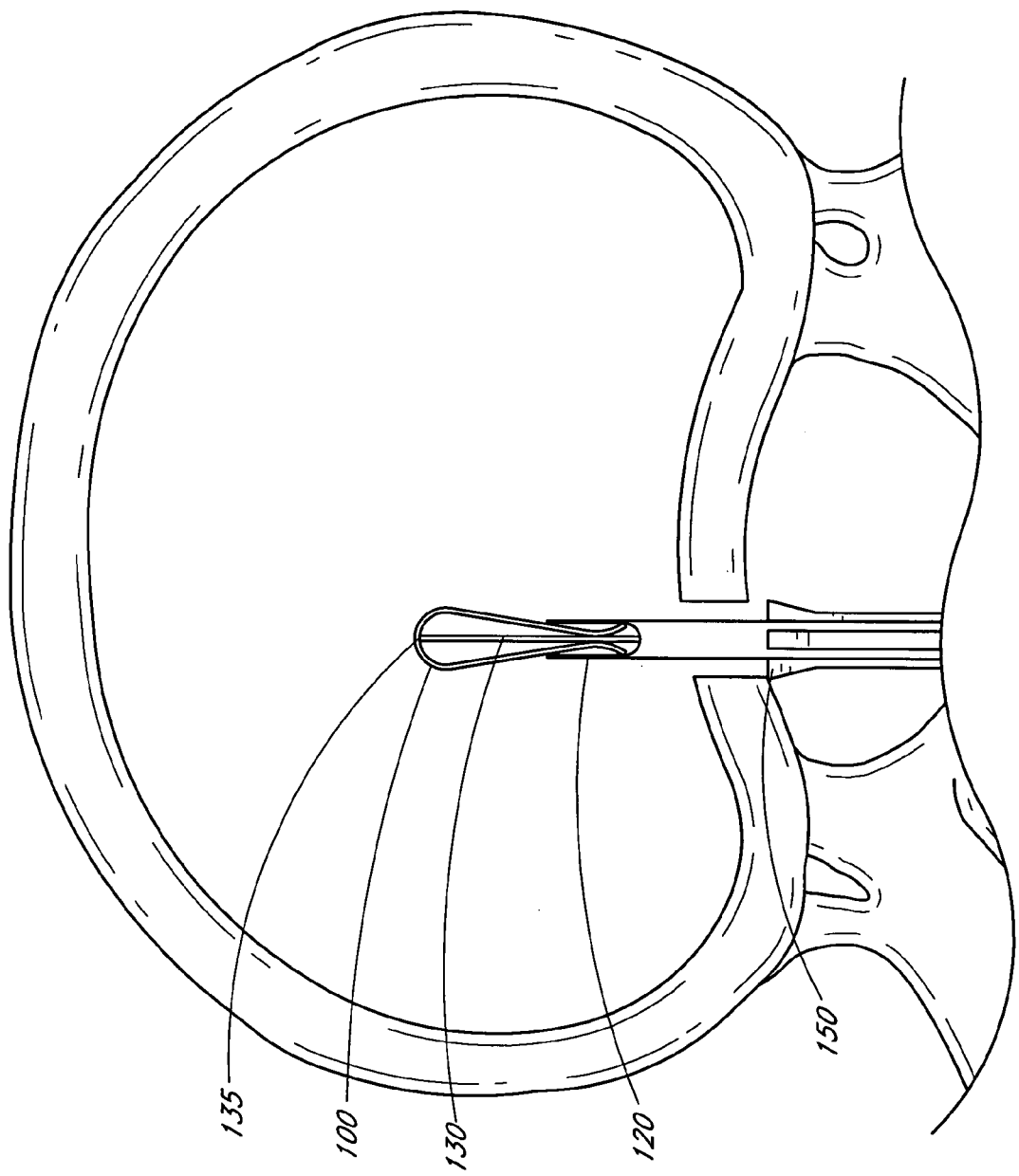
Figure 5D:
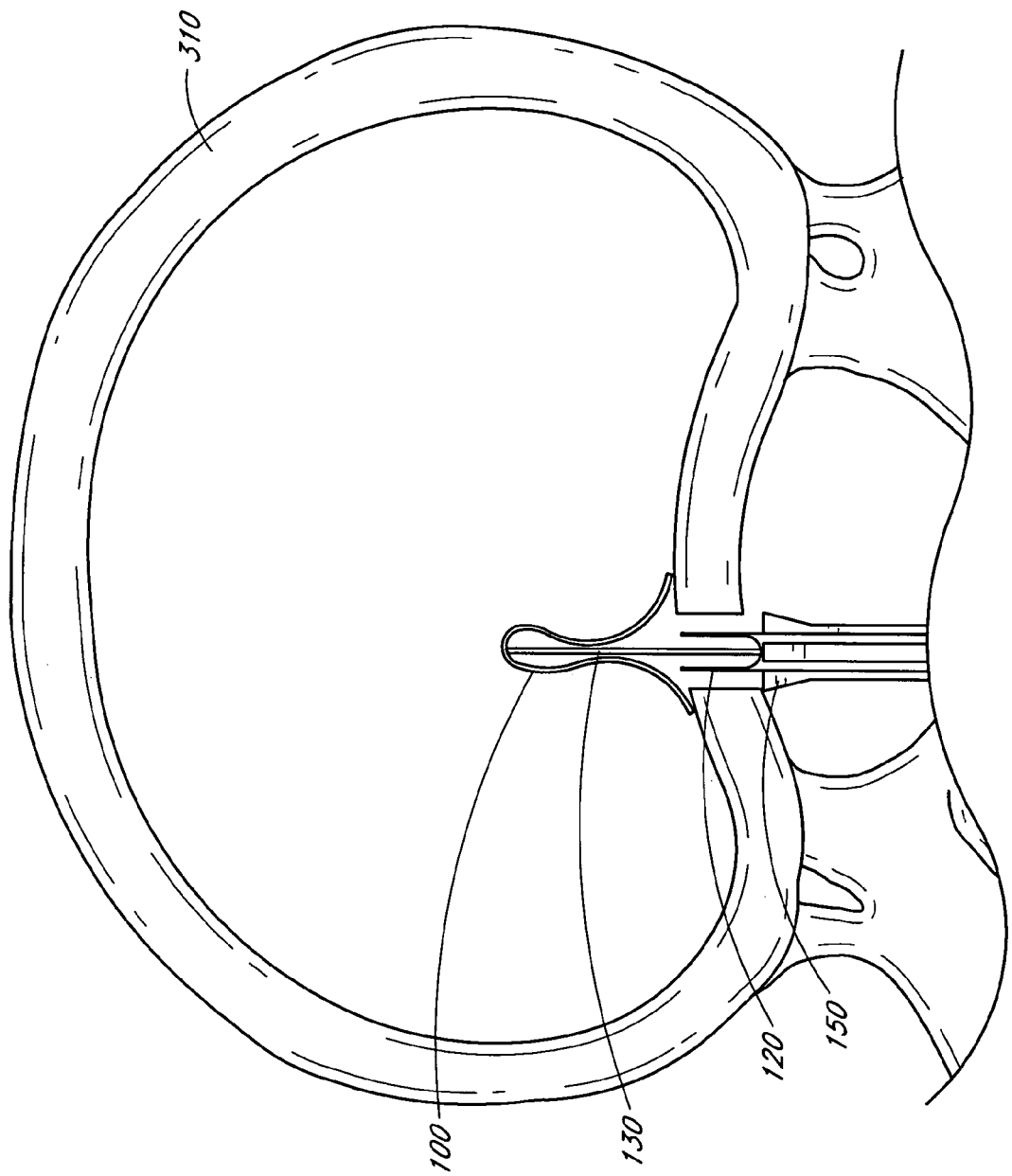

FIG. 5C shows the next step in the aforementioned method wherein the cannula 115 is rotated 90 degrees (after clearing the anulus). FIG. 5D shows the implant already unfolding or otherwise changing its transverse profile. In one embodiment, as shown, the gap between the opposing ends of the implant 100 is increasing as is the angle of the fold created at the implant/advancer coupling member 135. As discussed earlier this initial unfolding can be the product of a variety of factors including the inherent resiliency of the implant 100 or the coupling member 135.

Figure 5E:
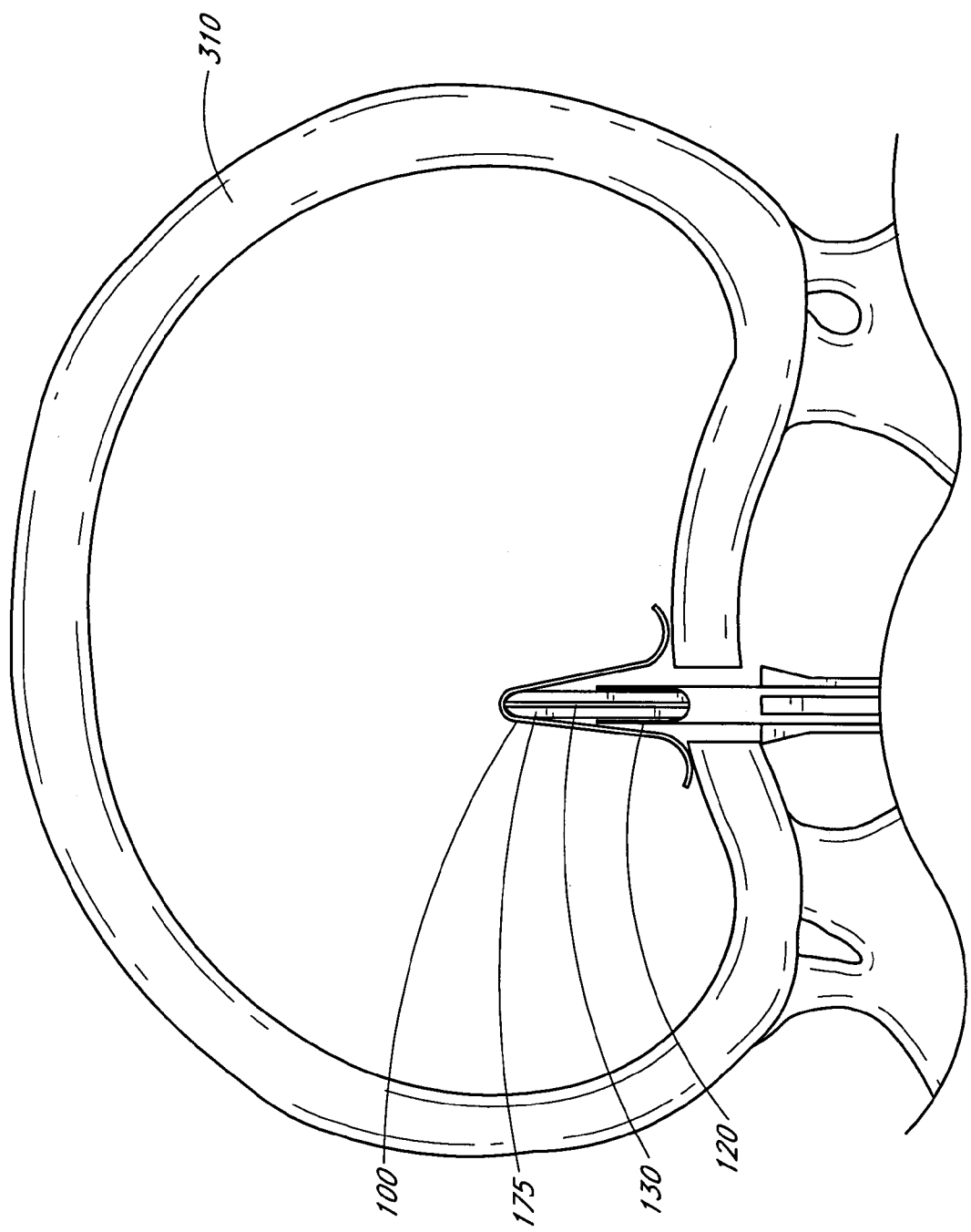
Figure 5F:
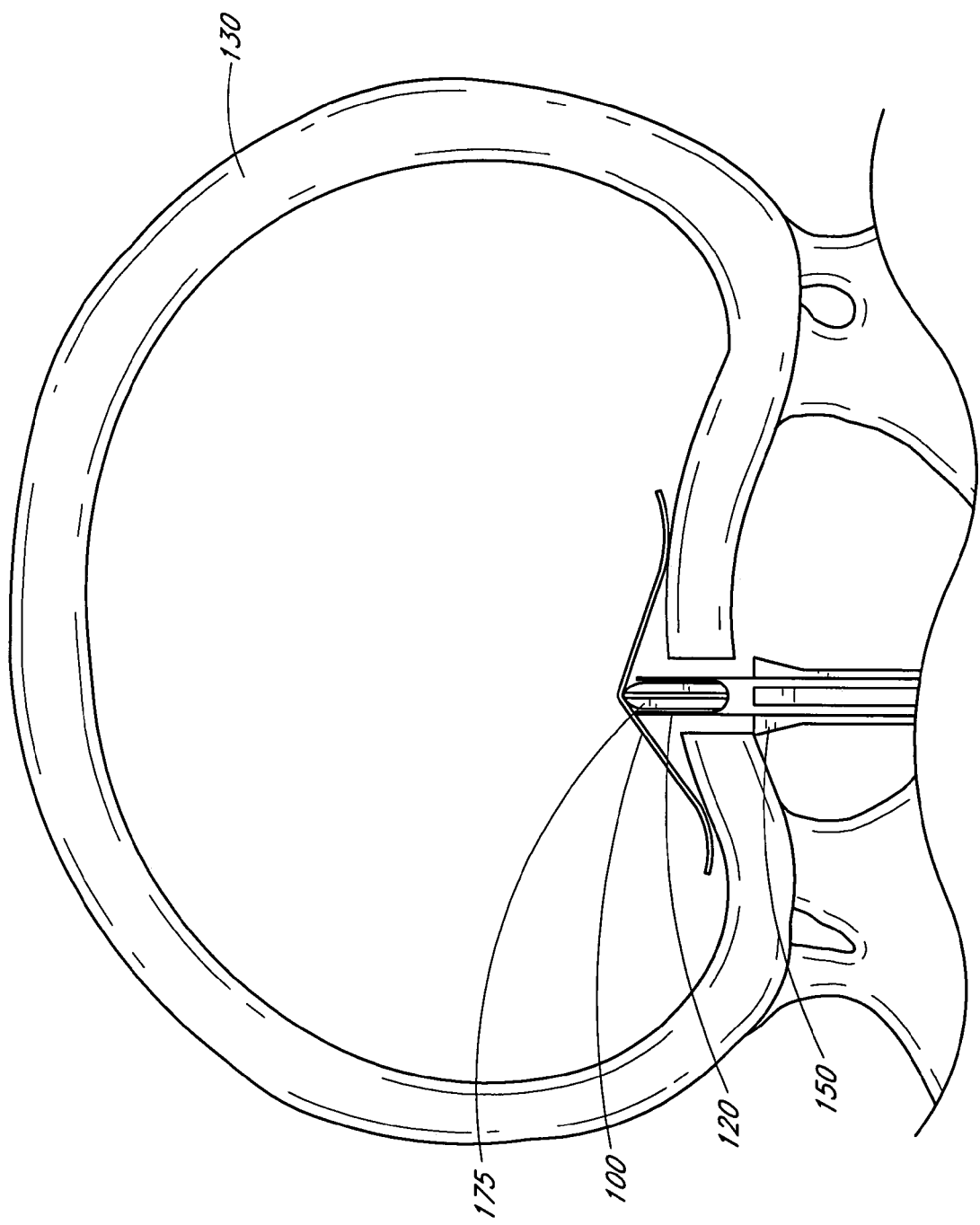

FIG. 5E shows the advancement of wedge-tipped expanders 175 which can aid or replace the initial unfolding step described above. The expanders 175, in one embodiment, are wedge-tipped. In other embodiments, the expanders can be shaped in any form that permit sufficient contact with the implant to lever it open or otherwise reconfigure it, including but not limited to flat or rounded shapes. Additionally, other embodiments may include expanders comprising balloons, springs, elastic members, or mechanical linkages adapted to expand or reconfigure the implant FIGS. 5F shows the advancement of the cannula tip 120, 120' to assist the expanders in opening the implant 100. In one embodiment, advancer 130, expander 175, and implant 100 can be retracted against the distal end of cannula 120 and implant 100. Force between cannula tip 120 and implant 100 acts to expand implant 100 while minimizing forces between implant 100 and the anular wall. This retraction of implant 100, advancer 130, and expander 175 can be done at a different rates or snychronized or to different extents relative to the retraction of cannula 120 to generate this force and/or open implant 100 to a greater or lesser extent during retraction of implant 100. In one embodiment, this opening step is particularly advantageous in instances where the tissue surface upon which the implant is to be positioned in weakened and would otherwise provide a poor deflection surface or if the defect is large such as would allow the implant to be pulled back through the defect instead.

Figure 5G:
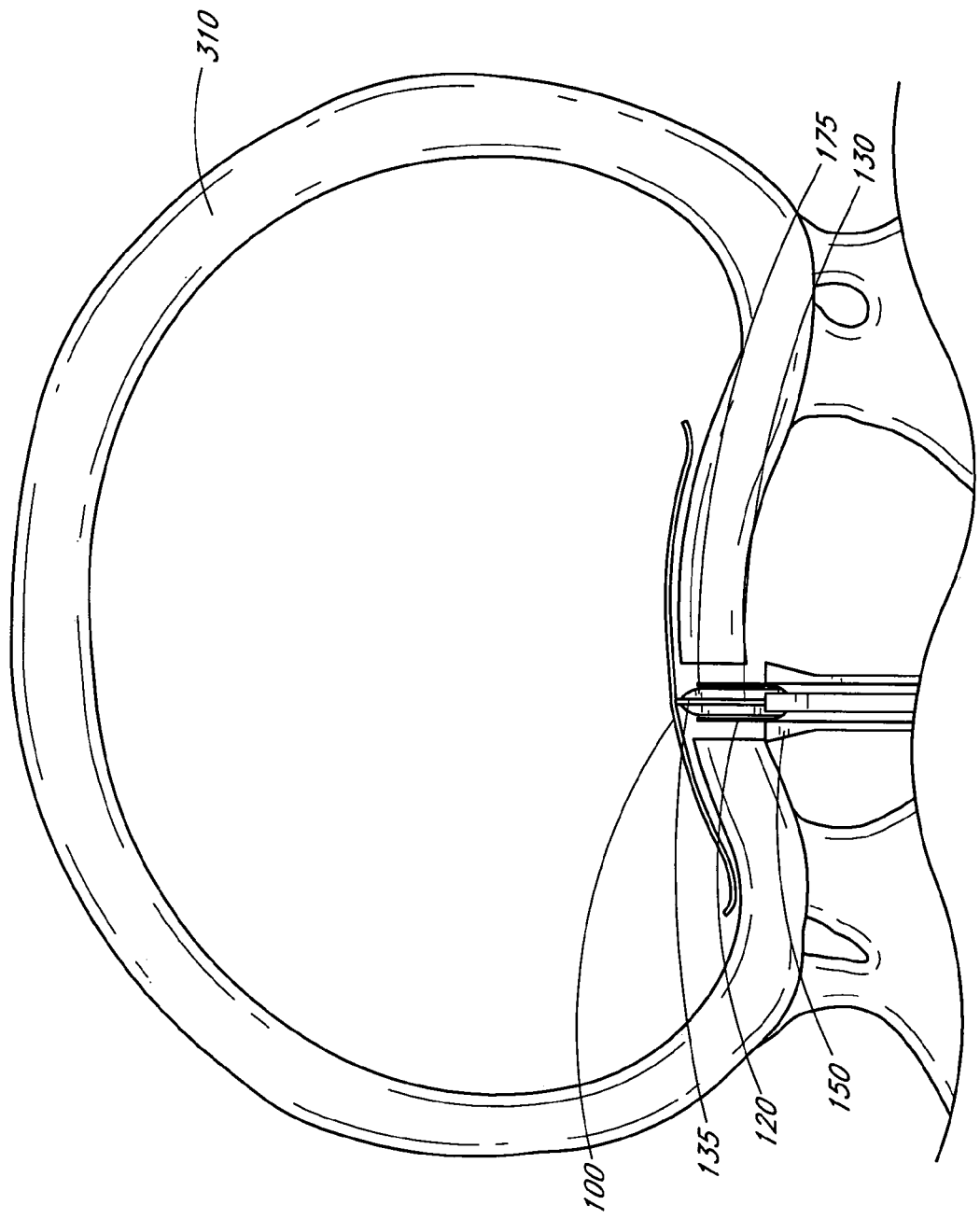
Figure 6:
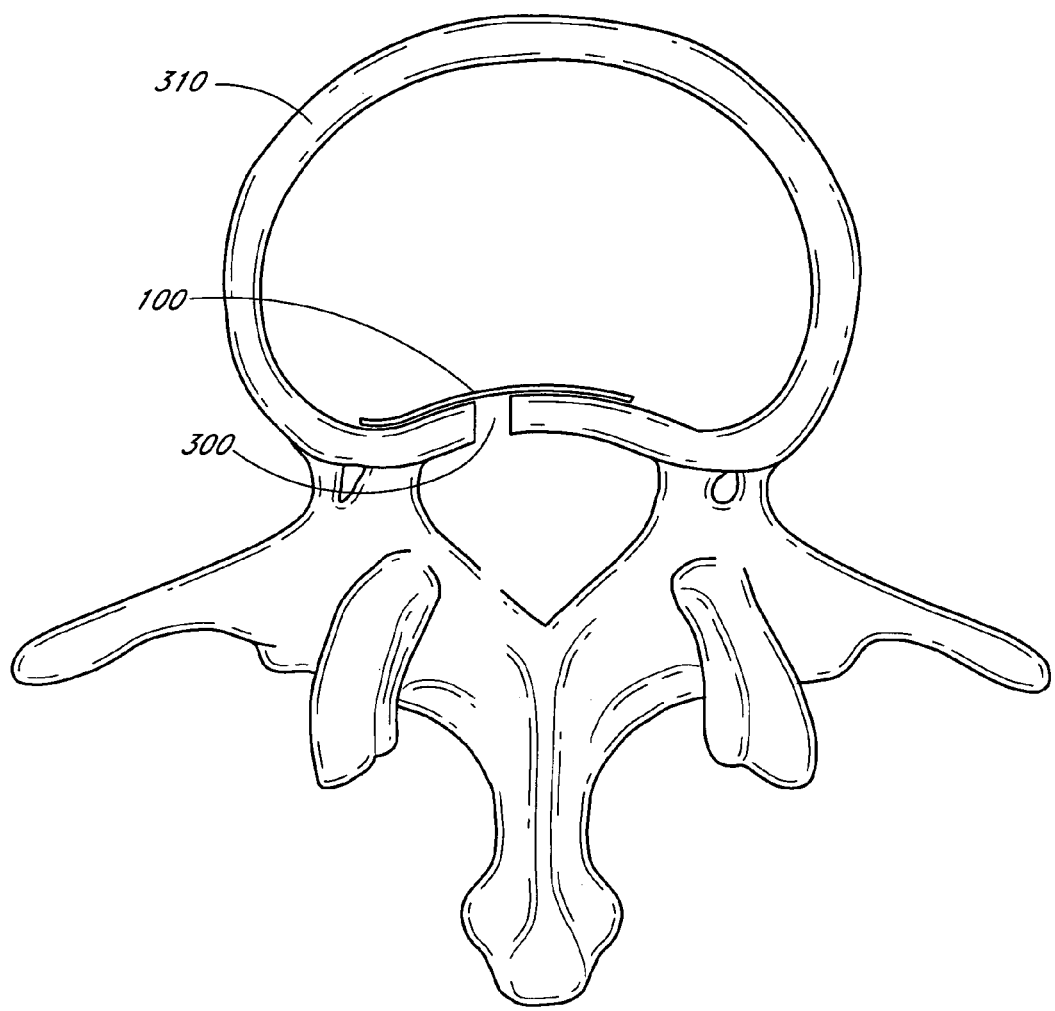
FIG. 6 is an axial view of the cross-section of an intervertebral disc showing an implant situated along the posterior of the anulus and implanted relative to a defect.

FIG. 5G show the final steps of delivery, in one embodiment, wherein the implant 100 is pulled towards the posterior of the anulus 310 as the ends of the implant 100 are deflected and advanced laterally along its inner surface. This posterior travel can be caused when the advancer 130, cannula 120, and expander 175 are retracted in unison. At this point the coupling member 135 is disengaged from the implant 100 and the device is removed from the patient. Note that, in one embodiment that substantially throughout the procedure the depth stop 150 maintains relative position so that the surgeon is certain of the placement of the device along the anulus surface. The retraction of the various elements of the system can be coordinated relative to depth stop 150 to minimize forces on surrounding tissues or optimize expansion or position of implant 100 relative to defect 300. FIG. 6 shows a fully implanted device 100.(this implant being sized to cover the entire posterior anulus) and the blocked-off defect 300.

Figure 7A:
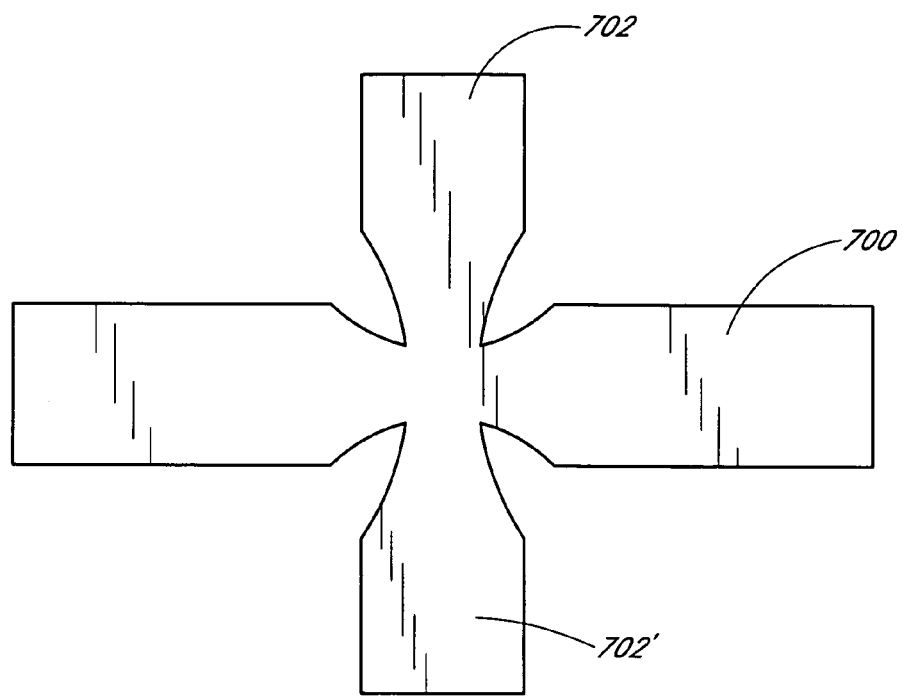
FIGS. 7A-7D show aspects of the implant.
Figure 7B:
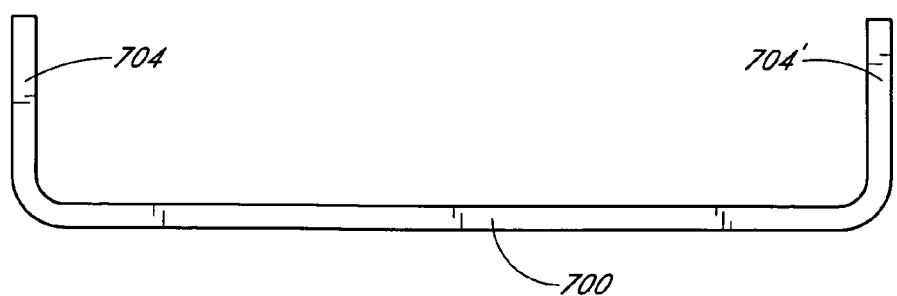
Figure 7C:
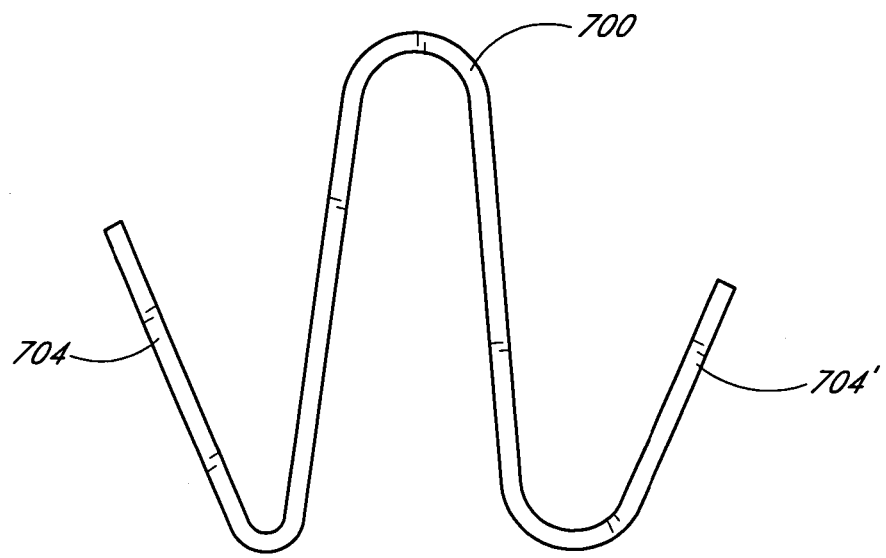
Figure 7D:
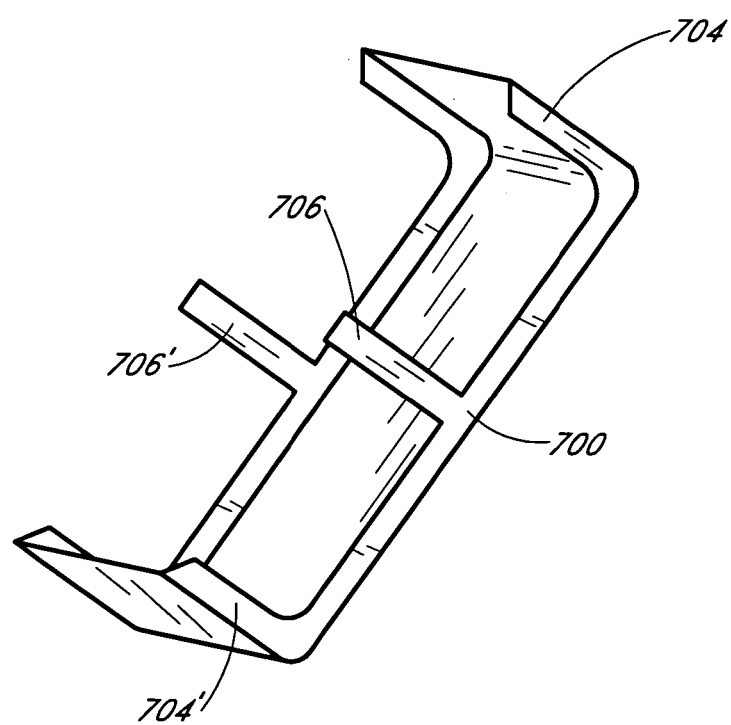

In several embodiments, relatively simple rectangular meshes or patches are provided for implantation. In other embodiments, more complex devices can be used, including, but not limited to stents, grafts, arterial septal defect closure devices and the like. FIG. 7A shows an elongated implant 700 with two vertical extensions 702, 704 that can be oriented, folded, and expanded according to the teachings of various embodiments of the invention. FIG. 7B shows an implant with lateral extensions 702, 704' as might be used to cover the posterior and lateral walls of an anulus. FIG. 7C shows the implant 700 exhibiting multiple folds along its long axis to compress its delivery profile. Finally, FIG. 7D presents a concave elongate member that has lateral extensions 702, 704' and midline lateral extensions 706, 706'. This design also permits folding and compression along one or more axes and can be delivered according to the teachings herein.

As part of an implantation procedure according to one embodiment of the invention, active and passive systems can be incorporated into the delivery devices or the implants to aid the in preparation of the delivery site or in manipulating the implant. For instance, in one embodiment, a gas, liquid and/or solid component can be added to the implant during positioning or after positioning to further reshape the implant or adjust its size. In some embodiments, the implant comprises one or more pharmaceutical agents. The pharmaceutical agent can facilitate pain reduction or inhibition of scarring, and can include genetically active growth or healing factors. In a further embodiment, lubrication is provided to reduce friction as the implant exits the delivery device. One or more pharmaceutical agents can also be provided by or through the cannula or advancer. In yet another embodiment, materials that aid in the visualization of the implant are provided, including, but not limited to, material for radio opaque location through a radiograph. Visual markers can be located on the implant and/or the delivery device.

In one embodiment, the implant can be anchored to adjacent or nearby tissue and an anchoring mechanism, such as a stapler, can be incorporated into the delivery device. In another embodiment, a mechanism for activating an anchoring mechanism can be contained within the implant itself. Heat, energy delivery from the electromagnetic spectrum, or the removal of heat (chilling or freezing) can be employed before, after or during the implant deployment to aid in positioning, function of the implant, or related disc or spine treatments such as the vaporization of unwanted tissue, the deadening of pain receptors, and the removal of bone or scar tissue. In one embodiment, means for adjusting the temperature of surrounding tissue is coupled to or integral with the delivery device. In another embodiment, means for adjusting temperature is an instrument that is separate from the delivery device.

In some embodiments, a delivery device comprises one or more axially extending lumens, for placing the proximal end of the device in fluid communication with the distal end, for any of a variety of purposes. For example, one or more lumens can extend through the advancer 130. Alternatively or in addition, the outside diameter the advancer can be dimensioned smaller than the inside diameter of the delivery cannula 115 to create an annular space as is well understood in the catheter arts. A first lumen can be utilized for introduction of radiopaque dye to facilitate visualization of the progress of the implant 100 and or distal end 2 of the device 200 during the procedure. The first lumen or second lumen can be utilized to introduce any of a variety of media. In one embodiment, one or more lumens are used to deliver saline solution. In another embodiment, one or more lumens are used to deliver pharmaceutical agents, including but not limited to, anti-inflammatory agents, steroids, growth factors (such as TNf-α antagonists), antibiotics, vasodilators, vasoconstrictors, and functional proteins and enzymes (such as chymopapain). In one embodiment, one or more lumens is used to aspirate material, such as biological fluids or nucleus pulposus. In another embodiment, one or more lumens is used to introduce nucleus augmentation material, or other biological or bio-compatible material, before, during or at the end of the procedure. In several embodiments, one or more lumens are used to deliver fluid, or other material, to a site to aid in heating or cooling the site tissue.

While this invention has been particularly shown and described with references to preferred embodiments thereof, it will be understood by those skilled in the art that various changes in form and details may be made therein without departing from the scope of the invention encompassed by the appended claims. In addition, one of skill in the art will understand that the steps recited in some embodiments need not be performed sequentially or in the order disclosed.

What is claimed is:

1. A method of delivering and positioning an implant within or adjacent to intervertebral disc tissue comprising:
   providing a delivery device comprising a proximal end for handling by a user and a distal end comprising a restraining member or sleeve for restraining a compressed implant;
   wherein said delivery device further comprises an advancer for advancing said implant relative to said sleeve wherein said advancer travels within, concentrically over, or alongside said sleeve;
providing a compressible implant having one or more limiting dimensions;
compressing said implant along said one or more limiting dimensions;
constraining said implant with said restraining member;
inserting the distal end of said delivery device within intervertebral disc tissue beyond an innermost surface of an anulus lamella,
wherein said implant is rotatable relative to the limiting dimension to achieve a diminished profile;
rotating said implant beyond the innermost surface of an anulus lamella to a desired orientation;
advancing said implant out of said sleeve, wherein said implant is folded;
allowing said implant to partially expand;
causing relative motion between the advancer and sleeve such that said sleeve contacts one or more surfaces of the folded implant thereby causing further expansion of said implant;
retracting said advancer and implant toward said innermost lamella of the anulus, thereby causing the implant to advance laterally along said surface and fully expand;
releasing the restraining member;
positioning the implant beyond the innermost lamella of an anulus; and
removing the delivery device.

2. The method of claim 1, wherein the step of compressing the implant comprises folding of the implant along one or more axes.

3. The method of claim 1, wherein expansion of the implant is achieved through unfolding of the implant along one or more axes.

4. The method of claim 1, wherein the step of compressing the implant comprises a step selected from the group consisting of one or more of the following: deflating, compacting, compressing, closing and condensing the implant.

5. The method of claim 1, wherein the implant expansion comprises a step selected from the group consisting of one or more of the following: inflating, enlarging, swelling, and opening the implant.

6. The method of claim 1, wherein the advancer is releaseably coupled to the implant.

7. The method of claim 1, wherein the restraining member partially restrains the implant.

8. The method of claim 1, wherein said implant expands due to inherent resiliency.

9. The method of claim 1, wherein said implant is substantially rectangular.

10. The method of claim 1, wherein said implant is selected from a group of materials consisting of one or more of the following materials: nitinol, steel, and polymer.

11. The method of claim 1, wherein said implant comprises collagen or small intestine submucosa.

12. The method of claim 1, wherein said implant comprises seeded tissue.

13. The method of claim 1, wherein said implant comprises unseeded tissue.

14. The method of claim 1, wherein said implant comprises a barrier.

15. The method of claim 1, further comprising anchoring said implant to said intervertebral tissue.

16. The method of claim 1, further comprising activating an anchoring mechanism within said implant, thereby anchoring said implant to the disc.

* * * * *